(12) United States Patent
Dejonge

(10) Patent No.: US 11,594,329 B2
(45) Date of Patent: Feb. 28, 2023

(54) PROGRAMABLE, REFILLABLE MEDICATION PACKAGE WITH SCHEDULED METERED DISPENSING AND MED UNIT SENSOR

(71) Applicant: Stuart W Dejonge, Lake Mary, FL (US)

(72) Inventor: Stuart W Dejonge, Lake Mary, FL (US)

(73) Assignee: DEJONGE ASSOCIATES INC, Lake Mary, FL (US)

( * ) Notice: Subject to any disclaimer, the term of this patent is extended or adjusted under 35 U.S.C. 154(b) by 394 days.

(21) Appl. No.: 16/873,036

(22) Filed: Jan. 22, 2020

(65) Prior Publication Data
US 2021/0225503 A1    Jul. 22, 2021

(51) Int. Cl.
| | |
|---|---|
| *G16H 40/67* | (2018.01) |
| *G05B 19/042* | (2006.01) |
| *G16H 20/13* | (2018.01) |
| *G16H 40/40* | (2018.01) |
| *G06K 7/10* | (2006.01) |
| *A61J 7/00* | (2006.01) |
| *A61J 7/04* | (2006.01) |

(52) U.S. Cl.
CPC ............ *G16H 40/67* (2018.01); *A61J 7/0076* (2013.01); *A61J 7/0418* (2015.05); *A61J 7/0427* (2015.05); *A61J 7/0445* (2015.05); *A61J 7/0481* (2013.01); *G05B 19/042* (2013.01); *G06K 7/10297* (2013.01); *G16H 20/13* (2018.01); *G16H 40/40* (2018.01); *G05B 2219/25419* (2013.01)

(58) Field of Classification Search
CPC ........ G16H 40/67; G16H 40/40; G16H 20/13; G05B 19/042; G05B 2219/25419; G06K 7/10297; A61J 7/0076; A61J 7/0418; A61J 7/0427; A61J 7/0445; A61J 7/0481
See application file for complete search history.

(56) References Cited

U.S. PATENT DOCUMENTS

| | | | |
|---|---|---|---|
| 4,490,711 | A | 12/1984 | Johnston |
| 4,588,303 | A | 5/1986 | Wirtschafter et al. |
| 4,663,621 | A | 5/1987 | Field et al. |
| 4,725,997 | A | 2/1988 | Urquhart et al. |
| 4,748,600 | A | 5/1988 | Urquhart |
| 4,768,177 | A | 8/1988 | Kehr et al. |
| 4,942,544 | A | 7/1990 | McIntosh et al. |
| 5,142,484 | A | 8/1992 | Kaufman et al. |

(Continued)

*Primary Examiner* — Michael Collins

(57) ABSTRACT

A programmable, refillable medication dispenser with scheduled metered medication unit dispensing, includes a main housing, a powered CPU with countdown timer, a multi-unit medication removable refillable cartridge with a (first) lock, a medication release control gate positioned at a medication outlet and connected to a (second) lock being a gate control mechanism, and an in-chamber medication unit sensor. A pharmacist will insert a medicine cartridge into the main housing, locking it in, and will program the CPU to permit a patient to activate dispensing according to a predetermined schedule, and then only when a medication unit is sensed in the chamber. A patient may receive the dispenser and activate medication dispensing according to the programmed schedule and dispense by the timer schedule, only when a medication unit is sensed in the chamber.

20 Claims, 13 Drawing Sheets

(56) References Cited

U.S. PATENT DOCUMENTS

| | | | | |
|---|---|---|---|---|
| 5,200,891 | A | 4/1993 | Kehr et al. | |
| 5,230,441 | A | 7/1993 | Kaufman et al. | |
| 5,630,347 | A * | 5/1997 | Elvio | G07F 11/68 83/210 |
| 5,755,357 | A * | 5/1998 | Orkin | A61J 7/0084 221/121 |
| 6,163,737 | A | 12/2000 | Fedor et al. | |
| 6,601,729 | B1 * | 8/2003 | Papp | B65D 83/0454 221/25 |
| 7,751,932 | B1 | 7/2010 | Fedor et al. | |
| 7,767,093 | B2 | 8/2010 | Frank | |
| 8,135,497 | B2 * | 3/2012 | Joslyn | A61J 7/0076 700/242 |
| 8,453,874 | B2 | 6/2013 | Simpson et al. | |
| 8,600,548 | B2 * | 12/2013 | Bossi | A61J 7/0084 700/231 |
| 9,007,875 | B2 | 4/2015 | Nurse et al. | |
| 9,351,907 | B2 * | 5/2016 | Luoma | A61J 7/04 |
| 9,558,596 | B2 | 1/2017 | Nurse et al. | |
| 10,176,663 | B2 * | 1/2019 | King | A61J 7/04 |
| 10,512,592 | B1 * | 12/2019 | Sandhu | G07F 11/005 |
| 2005/0205598 | A1 * | 9/2005 | Gelardi | B65D 83/0409 221/266 |
| 2007/0093935 | A1 * | 4/2007 | Fu | G16H 20/10 700/237 |
| 2007/0185615 | A1 * | 8/2007 | Bossi | A61J 7/0084 700/244 |
| 2011/0295416 | A1 * | 12/2011 | Aquilonius | A61J 7/0481 221/98 |
| 2012/0145740 | A1 * | 6/2012 | Chu | B65D 83/0409 221/277 |
| 2014/0103063 | A1 * | 4/2014 | Yuyama | G07F 17/0092 221/306 |
| 2019/0244510 | A1 * | 8/2019 | Mehregany | A61J 1/035 |
| 2020/0077706 | A1 * | 3/2020 | Wilson | A61M 15/008 |
| 2020/0383873 | A1 * | 12/2020 | Dejonge | A61J 7/0481 |

\* cited by examiner

PROGRAMABLE, REFILLABLE MEDICATION PACKAGE WITH SCHEDULED METERED DISPENSING AND MED UNIT SENSOR

REFERENCE TO RELATED APPLICATIONS

The present application is a continuation-in-part of United States co-pending utility application Ser. No. 16/501,745, filed on Jun. 4, 2019, and titled "Programmable, Refillable Medication Package With Scheduled Metered Dispensing" by the same inventor herein.

BACKGROUND OF INVENTION a. Field of Invention

The present invention generally relates to devices for the distribution/release of medication to patients that are especially beneficial for the timed controlled release of medication that may be either dangerous or addictive or both, e.g., for the timed release of opioids and patient-controlled chemotherapy. Thus, the present invention is directed to devices that receive safe cartridges of medication dosages, to be released on a timed schedule and only when a sensor senses a medication unit in a dispensing chamber. The present invention devices are thus dispensers that include two separate locks, one being a multi-unit medication cartridge lock functionally connected to a central processing unit and positioned adjacent a cartridge receiver for locking and unlocking the medication cartridge (so that it is secure except for a professional access, such as a pharmacist, dispensary agent or nurse), and the other being a control gate mechanism (lock) connected to the CPU and to a medication release control gate to permit or prohibit activation of the gate for medication dosage release according to a timer in conjunction with a med unit sensor. These present invention devices are adaptable for use with pills, capsules and other solid units, and the release chutes may be structured to hold only one medication unit or two.

b. Description of Related Art

The following patents are representative of the field pertaining to the present invention:

U.S. Pat. No. 9,558,596 to Nurse et al describes dosing times for medication that may be tracked by taking into account preset dosing sequences and when users indicate that they have taken the medication. The medication may also be kept in its original container. An encoder disk may be attached to a medicine container. The encoder disk may be encoded with a dosing frequency that indicates how frequently the medication should be taken, as well as any other desired information. A base station may be configured to accept and hold one or more medicine containers. The base station may be configured to read the encoded dosage from the encoder disk, an RFID tag, a barcode, or another component capable of conveying dosing information, and detect when the medicine container is removed from and placed on the base station. The base station may also include various indicators of its current state.

U.S. Pat. No. 9,007,875 to Nurse et al describes a medicine station or stand-alone alert device that has a processor having access to memory, wherein the memory stores a control module, and the processor is configured to execute the modules stored in the memory. The medicine station or stand-alone alert device also includes one or more indicators. The control module is configured to periodically check for an external notification from a primary alert device that it is time to take a medication. Upon receiving the external notification, the control program is configured to cause the medicine station or stand-alone alert device to enter an amplified alert mode with respect to the primary alert device via the one or more indicators.

U.S. Pat. No. 8,453,874 to Simpson et al describes a dispenser and method for dispensing pills to patients from cartridges featuring downloadable remotely programmable timer and network communications links, alerting timer, databasing, printer, and battery.

U.S. Pat. No. 7,751,932 to Fedor et al describes a system for monitoring and dispensing medical items that includes a plurality of hook registers. Each of the hook registers includes sensors sensing the removal or addition of a medical item to the storage location on the hook register. Each hook register has a microprocessor connected to the sensor which stores a count of the items added or removed from the location. The microprocessor also includes location identifying information specifically associated with the particular hook register. The microprocessor is periodically polled by a controller which reads and stores the count and location identifying information from each of the hook registers. The controller information is periodically read by a data terminal which is connected through a local area network to a remote computer having a processor and data store. A user of the data terminal is enabled to specify a patient for whom medical items will be used when the items are removed from the hook registers or other storage locations. In addition, the system also monitors inventories of items and levels of usage by users. The system also monitors and controls the dispense of other medical items from box registers as well as controls the dispense of items from secure storage locations such as electronic lock drawers and medicine dispensers.

U.S. Pat. No. 7,467,093 to Newton et al describes a method of tracking and dispensing medical items for use by patients associated with a health care institution that includes storing in a data store in connection with a computer data representative of patients and medical items prescribed for the patients. Authorized users such as a nurse, are enabled to dispense prescribed items for patients through medical item dispensers. A record is included in the data store that the medical items have been dispensed. In an exemplary system medical items that have been dispensed are tracked to the point of giving the item to the patients using portable terminals that are carried to the bedside of the patients. The activity of giving the appropriate medical item to each respective patient is recorded in the portable terminal as medical items are given to a plurality of patients. The data stored in the portable terminal concerning the giving of medical items to patients is communicated through the system and stored in the data store to provide a record that the medical items which were dispensed for a patient were actually administered. In an alternative form of the system patients are enabled to dispense medications on an outpatient basis through a self-service medical item dispenser. In a method of operating such a system a benefit plan associated with the patient is determined from rules stored in connection with data representative of the benefit plan. Payment for dispensed medications is provided by the benefits provider associated with the patient's benefits plan and a co-payment is made by the patient from a credit or debit card account.

U.S. Pat. No. 6,163,737 to Fedor et al describes a medical item dispensing apparatus that includes a dispenser which encloses a plurality of magazines. Each magazine holds a plurality of medical items which in the preferred form of the invention are cylindrical containers. Each magazine includes an opening. A guide and a front gate member are positioned adjacent to the opening. A back gate member is positioned further inward from the opening than the front gate member. The front gate member and back gate member are moved in coordinated relation so that the front gate member enables a medical item adjacent the opening to pass through the opening while the back gate member moves to prevent the other medical items in the magazine from moving toward the opening. After the dispense of the medical item from the magazine the front gate member moves to block the passage of further medical items through the opening while the back gate member moves to enable medical items to move toward the opening. The magazines dispense medical items from the dispenser responsive to a user terminal. The user terminal is operatively connected to a computer which includes a data store which maintains data representative of medical items taken for patients.

U.S. Pat. No. 5,230,441 to Kaufman et al describes a system for dispensing medication that includes a dispensing device unto which a prepackaged cassette can be releasably installed. The cassette contains medication that has been prepackaged in individual pockets along a strip. The strip is wound between a supply reel and a take up reel within the cassette. A control mechanism associated with the dispensing device advances the strip within the cassette by winding the strip onto the take up reel, while unwinding the strip from the supply reel, and while moving a dispensing mechanism also associated with the device into contact with the strip for opening a medication pocket to expel the medication from the strip and out of the cassette.

U.S. Pat. No. 5,200,891 to Kehr et al describes a device for monitoring medication of a patient and for prompting the patient into certain medication taking schedule and/or certain programming steps and routines. The device has a plurality of compartments, each of which may store medication and an electrical signaling system to emit medication alert signals from time-to-time, each of which the signals indicates (a) that medication should be taken, (b) from which compartment the medication should be taken, (c) and the quantity of medication to be taken. If a designated compartment is not opened and closed within a predetermined period of time, the electrical signaling system will sound an alarm. If each designated compartment is opened and closed, the take-medication signal and the alarm (if operating) are turned off and the event is recorded for later review. The device includes a display having a substantially continuous display area having portions thereof closely adjacent to each compartment.

U.S. Pat. No. 5,142,484 to Kaufman et al describes an interactive patient assistance device that houses first and second compartments for storing a first item and a second item away from access by the patient. First and second delivery mechanisms are associated with the first and second compartments for making the first stored item available to the patient in response to a first command signal and for making the second stored item available to the patient in response to a second command signal. The first and second items are delivered to the patient according to schedules stored in resident memory. The schedules may be altered by a prescribed command issued by the patient.

U.S. Pat. No. 4,942,544 to McIntosh et al describes a medication clock for producing a record of a patient in complying with a medication schedule. A data base is provided which stores the time and date of each medication that the patient takes including those medications taken in response to an alarm by the clock as well as medications taken by the choice of the patient. The dosage schedule may be programmed by reading of information written by the pharmacist.

U.S. Pat. No. 4,768,177 to Kehr et al describes a device for indicating when medication should be taken has plural compartments, each of which may store medication. An electrical signaling system emits take-medication signals from time to time, each of which said signals indicates (a) that medication should be taken, (b) from which compartment the medication should be taken, (c) the quantity of medication to be taken from the designated compartment, and instructions for taking the medication. If a designated compartment is not promptly opened and closed, the electrical signaling system will sound an alarm. If each designated compartment is opened and closed, the take-medication signal and the alarm (if operating) are turned off. A reload signal is given once a week, as a reminder to reload the compartments with medication. The device has modular construction. A first module has: (a) one of the compartments, (b) an alarm for producing an audible signal to alert the patient to take medication, (c) a timing signal generator for producing timing signals, (d) a circuit for energizing the alarm in response to selected timing signals, and (e) a switch for turning off said alarm when the medication has been taken from the container in the first module. Each remaining module is a plug-in device which has a compartment, receives timing signals from the first module, sends signals to activate said alarm in response to selected timing signals and a manual switch for deactivating said alarm when medication is taken from the compartment in the module.

U.S. Pat. No. 4,748,600 to Urquhart describes an interactive drug dispenser which actively controls the pattern in which doses of one or more pharmaceutical preparations are administered to a patient. The dispenser is programmed with information concerning an initial dosing regimen, and monitors deviations from that regimen. The dispenser is adapted to calculate from the dosage deviation a dosing error correction factor which corrects a patient's measured plasma drug concentration for deviations from a prescribed dosing regimen, so as to distinguish the effects of patients' dosing errors from suboptimal prescribed dosage regimens.

U.S. Pat. No. 4,725,997 to Urquhart describes a contingent dosing device which actively controls the pattern in which doses of one or more pharmaceutical preparations are administered to a patient. The device is programmed with information concerning an initial dosing regimen, and monitors deviations from that regimen. Based on the acceptability of the calculated deviations, the device may dispense or withhold medication. The invention also includes an automatic drug dosage compliance method using the contingent dosing device.

U.S. Pat. No. 4,663,621 to Field et al describes a medicine cabinet that has a housing and a door. The door is provided with an electrically operated lock which is operable by using the push keys. The opening code for the lock is initially set by inserting four keys into four holes in a four by ten array of holes provided in the casing on the inside of the door. The circuits for the code pre-setting and code inputting circuits are provided on a membrane. The cabinet is provided with a light emitting diode (LED) and a buzzer which can be operated by timing means at set intervals. The LED and the buzzer also operate while the door is open. Additional facilities may also be provided on the cabinet.

U.S. Pat. No. 4,558,303 to Fielden describes an analogue voltage-to-digital voltage converter that has a voltage divider with a plurality of stages each providing an output voltage for comparison with the unknown voltage and in addition provides interpolation between the output voltage to improve the accuracy. Interpolation is effected by adding a ramp voltage to the unknown ramping through a magnitude equivalent to the voltage of at least one stage. With one tap on the voltage divider selected, comparison of the unknown plus ramp voltage is effected successively as the voltage ramps. By noting when the combined voltage reaches the level of one of the divider output voltages and by counting the number of comparisons made from the time when the ramp voltage is at a predetermined magnitude and comparing this with the time taken to ramp through one or a plurality of whole divider stages, determination can be made of the magnitude of the unknown voltage to a fraction of a stage.

U.S. Pat. No. 4,490,711 to Johnston describes a structure provided for assisting a person in keeping track of appointments, times for taking medication or the times for turning on electrical equipment or such. The structure comprises an electronic circuit capable of generating signals representing up to N different pre-set times at which specific events are to occur where N is a selected positive integer such as 20. Switches are then provided, each switch corresponding on a one-to-one basis to a unique pre-set time, such that the user can set those switches corresponding to the pre-set times at which the user desires events to take place. An alarm is provided to indicate in sequence when the actual time corresponds to the pre-set time corresponding to each set switch. The user can only shut off the alarm when the alarm is sounding and the system will then automatically record the number of times during which the alarm has come on and the user has responded to the alarm by silencing it thereby to provide a cumulative count of total events to which the user has responded. A doctor can then check the cumulative count to ensure that a patient has presumptively taken medicines prescribed at selected times in accordance with the programmed schedule on the structure. Because the alarm can only be silenced when it is sounding, accidental silencing of the alarm at any time is prevented. The structure of this invention combines the convenience and ease of an electronic alarm system with the simplicity and permanence of a written record of events.

Notwithstanding the prior art, the present invention is neither taught nor rendered obvious thereby.

SUMMARY OF INVENTION

The present invention is directed to programmable, refillable medication dispensers with scheduled metered medication unit sensing and timed dispensing. Some embodiments of these devices include extra features, such as child resistant activation components; some include communications components, as well.

In some preferred embodiments, the present invention medication dispensers include: a) a main housing having an outer structure and a cartridge receiver for insertion and removal of a multi-unit medication cartridge, said cartridge receiver being positioned for alignment of said multi-unit medication cartridge with a medication outlet chamber; b) a medication outlet chamber within said main housing, with a medication outlet for controllably releasing a medication unit from said cartridge and from said chamber according to a programmed schedule; c) a medication unit sensor functionally connected to said medication outlet chamber and to a powered, programmable central processing unit; d) said powered, programmable central processing unit located in said main housing that includes sufficient hardware and software to include a programmable timer for scheduled permitting time and scheduled prohibiting time for dispensing a medication unit from said medication outlet chamber, and includes an override subprogram connected to said medication unit sensor wherein a medication unit can only be dispensed by the opening of a medication release control gate when both a medication unit is sensed in said medication outlet chamber by said sensor, and said timer is operating in a permitting time, and when either a medication unit is not sensed or when said timer is operating in a prohibiting time, said release control gate cannot be opened; e) a multi-unit medication cartridge lock functionally connected to said central processing unit and positioned adjacent to said cartridge receiver for locking and unlocking a cartridge; f) a gate control mechanism and said medication release control gate connected to said gate control mechanism, said medication release control gate being positioned at said outlet, and said control gate having a first position prohibiting medication unit dispensing by closing said gate when said timer is in a prohibiting time or when there is no medication unit sensed in said chamber, or both, and a second position permitting medication unit dispensing by opening said gate when said timer is in a permitting time and a medication unit is sensed in said chamber by said sensor; g) a power source connected to said programmable central processing unit; wherein, an authorized medication dispensing person will insert and lock a multi-unit medication cartridge into said cartridge receiver of said main housing and will program said central processing unit to permit a patient user to move a medication unit into said outlet chamber and to accomplish dispensing activation according to a predetermined schedule such that when medication dispensing is permitted and a medication unit is sensed in said chamber, said gate control mechanism may be activated and said control gate may be opened for dispensing, and when medication dispensing is prohibited or a medication unit is not sensed in said chamber, said gate control mechanism cannot be activated.

In some preferred embodiments of the present invention medication dispenser with scheduled metered medication unit dispensing, the dispenser further includes an externally exposed operate-indicator that has a first setting to indicate that said dispenser is inoperable and a second setting to indicate that said dispenser is operable for controllably releasing a medication unit from said dispenser. In some preferred embodiments of the present invention medication dispensers with scheduled metered medication unit dispensing, the indicator is selected from the group consisting of a visual indicator, and an audio indicator and combinations thereof.

In some preferred embodiments of the present invention medication dispensers with scheduled metered medication unit dispensing, the multi-unit medication cartridge lock includes a solenoid and lock bar having an extended lock position and a retracted unlock position, and in wherein said solenoid is functionally connected to said central processing unit.

In some preferred embodiments of the present invention medication dispensers with scheduled metered medication unit dispensing, the medication release control gate includes a gate wall and a gate solenoid functionally connector to said gate, said solenoid having an push bar that is operable only when said timer is in a permitting time and a medication unit is sensed in said chamber, said push bar having an extended position maintaining a locked gate and having a retracted position maintaining an unlocked gate.

In some preferred embodiments of the present invention medication dispensers with scheduled metered medication unit dispensing, the medication release control gate is selected from the group consisting of a slide gate, a rotatable gate, and a hinged gate. In some preferred embodiments of the present invention medication dispensers with scheduled metered medication unit dispensing, the medication release control gate is a slide gate.

In some preferred embodiments of the present invention medication dispensers with scheduled metered medication unit dispensing, there is further g) at least one patient user control component connected to said central processing unit and externally exposed for user dispensing activation that functions as a child resistant feature that must be activated to move said gate control mechanism to its second position, to permit medication unit dispensing by opening said gate.

In some preferred embodiments of the present invention medication dispensers with scheduled metered medication unit dispensing, the patient user dispensing control component is a button and said button operates in conjunction with said gate as a child resistant feature that must be activated to dispense medication.

In some preferred embodiments of the present invention medication dispensers with scheduled metered medication unit dispensing, there is a spring mechanism connected to said gate that biases said gate to its closed position.

In yet different embodiments of the present invention, the programmable, refillable medication dispenser with scheduled metered medication unit dispensing, includes: a) a main housing having an outer structure and a cartridge receiver for insertion and removal of a multi-unit medication cartridge, said cartridge receiver being positioned for alignment of said multi-unit medication cartridge with a medication outlet chamber; b) a medication outlet chamber within said main housing, with a medication outlet for controllably releasing a medication unit from said cartridge and from said chamber according to a programmed schedule; c) a medication unit sensor functionally connected to said medication outlet chamber and to a powered, programmable central processing unit; d) said powered, programmable central processing unit located in said main housing that includes sufficient hardware and software to include a programmable timer for scheduled permitting time and scheduled prohibiting time for dispensing a medication unit from said medication outlet chamber, and includes an override subprogram connected to said medication unit sensor wherein a medication unit can only be dispensed by the opening of a medication release control gate when both a medication unit is sensed in said medication outlet chamber by said sensor, and said timer is operating in a permitting time, and when either a medication unit is not sensed or when said timer is operating in a prohibiting time, said release control gate cannot be opened; e) a multi-unit medication cartridge lock functionally connected to said central processing unit and positioned adjacent to said cartridge receiver for locking and unlocking a cartridge; f) a gate control mechanism and said medication release control gate connected to said gate control mechanism, said medication release control gate being positioned at said outlet, and said control gate having a first position prohibiting medication unit dispensing by closing said gate when said timer is in a prohibiting time or when there is no medication unit sensed in said chamber, or both, and a second position permitting medication unit dispensing by opening said gate when said timer is in a permitting time and a medication unit is sensed in said chamber by said sensor; g) a power source connected to said programmable central processing unit; h) a communication mechanism connected to said control processing unit and adapted to communicate with a separate programming device for at least performing one of: (a) locking and unlocking a multi-unit medication cartridge; (b) permitting and prohibiting unlock time frames for said timer and (c) coupling a power transmission to said dispenser; wherein, an authorized medication dispensing person will insert and lock a multi-unit medication cartridge into said cartridge receiver of said main housing and will program said central processing unit to permit a patient user to move a medication unit into said outlet chamber and to accomplish dispensing activation according to a predetermined schedule such that when medication dispensing is permitted and a medication unit is sensed in said chamber, said gate control mechanism may be activated and said control gate may be opened for dispensing, and when medication dispensing is prohibited or a medication unit is not sensed in said chamber, said gate control mechanism cannot be activated. In some of these embodiments, the communication mechanism is selected from the group consisting of a wire port and a wireless transmitter receiver. In some of these embodiments, the communication mechanism includes both a wire port and a wireless transmitter receiver. In some of these embodiments, the device further includes an externally exposed operate indicator that has a first setting to indicate that said dispenser is inoperable and a second setting to indicate that said dispenser is operable for controllably releasing a medication unit from said cartridge. The indicator may be selected from the group consisting of a visual indicator, and an audio indicator and combinations thereof. In some embodiments, the audio indicator is an audio alarm.

In some of these embodiments with a communication mechanism, the multi-unit medication cartridge lock includes a solenoid and lock bar having an extended lock position and a retracted unlock position, and in wherein said solenoid is functionally connected to said central processing unit.

In some of these embodiments with a communication mechanism, the medication release control gate includes a gate wall and a gate solenoid functionally connector to said gate, said solenoid having a push bar that is operable only when said timer is in a permitting time and a medication unit is sensed in said chamber, said push bar having an extended position maintaining a locked gate and having a retracted position maintaining an unlocked gate.

In some of these embodiments with a communication mechanism, the medication release control gate is a slide gate.

In some of these embodiments with a communication mechanism, there is further i) at least one patient user control component connected to said central processing unit and externally exposed for user dispensing activation that functions as a child resistant feature that must be activated to move said gate control mechanism to its second position, to permit medication unit dispensing by opening said gate.

In some of these embodiments with a communication mechanism, the communication mechanism is a wireless transmitter receiver. In some of these embodiments with a communication mechanism, the communication mechanism wireless transmitter receiver is an NFC reader.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE SEVERAL VIEWS OF THE DRAWINGS(S)

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE EMBODIMENTS

Figure 1:
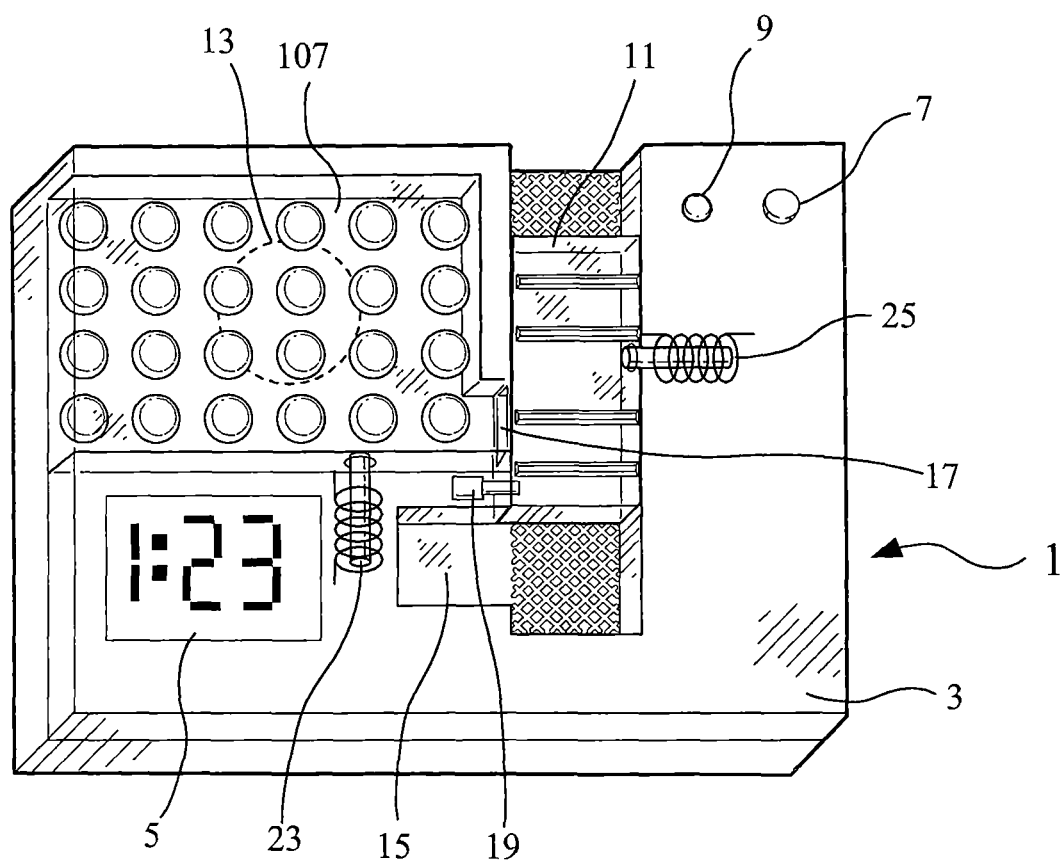
FIG. 1 shows a top view of one embodiment of a present invention programmable, refillable medication dispenser with scheduled metered medication unit dispensing and med unit sensing.

The present invention is directed to unit dosage medicine dispensing devices that receive cartridges of medication dosages to be released on a timed schedule. The cartridges are safe because they are locked and are thus set up to deny access for medication abuse. The present invention dispenser devices include two separate locks, one being a multi-unit medication cartridge lock functionally connected to a CPU and positioned adjacent a cartridge receiver for locking and unlocking the medication cartridge (ergo, secure except for a professional access, such as a pharmacist, dispensary or nurse), and the other lock being a control gate mechanism connected to the CPU and to a medication release control gate (such as a toggle) to permit or prohibit activation of the gate for medication dosage release according to a timer. The present invention medication unit sensor insures that the devices do not open for dispensing if a medication unit is not present in the outlet chamber.

The following is an example of how a present invention preferred dispenser device would work: a doctor would give the user patient a prescription for opioids or other dangerous drug, and the user patient would bring this script to the pharmacist. The pharmacist would take an empty cartridge and fill it with the correct opioid or other medicine, or would take a full cartridge from a pharma manufacturer. This cartridge would be color coded to a properly sized gate (e.g., a slide gate). The pharmacist would then insert the Cartridge into the present invention device and lock it in place. He would do programming or have a preset program transmitted to the device and thus set the CPU programmable timer to allow or disallow dispensing according to a preset regimen schedule. Both the cartridge and the gate would be locked in place and could not be removed without breaking the device.

The pharmacist would then, using his computer, check and confirm the programming with the prescription's dosing instructions. The complete package would then be given to the user patient for use after instruction by the pharmacist. A display clock on the unit (a countdown clock is preferred) would tell the user patient when he could access a tablet. The user patient sees the clock count down to zero, at which time the CPU would activate a gate with a solenoid or equivalent mechanism) for medication release only if the med unit sensor recognizes the presence of a med unit in the outlet chamber; if not, the gate could not open. The patient would have, for example, 1 hour to access the dose or the unit would automatically re-lock until the next dose is due. To access a tablet, the user patient would tilt the unit, allowing a single tablet to enter the outlet chamber, then push to slide open the gate and one tablet would be dispensed. The gate is preferably spring loaded and, when released by the user patient, it would automatically re-lock until the next dose is due.

When the cartridge is empty, the user patient would bring the device back to the pharmacy for either a re-fill or return of the deposit on the unit. If the dispenser or cartridge shows damage or tampering evidence, the refund would not be issued and a re-fill would not be honored. In preferred embodiments, the device housing, the gate, the outlet chamber and the Cartridge will be made of clear plastic, allowing the user patient to see the tablet move to the slot in the outlet chamber for dispensing. Also, in some preferred embodiments, an additional button must be pushed to open the gate, and this creates a simultaneous dual action child resistant requirement.

FIG. 1 shows an oblique top view of one embodiment of a present invention programmable, refillable medication dispenser 1 with scheduled metered medication unit dispensing as set by the pharmacy in accordance with a prescription. Dispenser 1 includes a main housing 3, a cartridge 107, a cartridge solenoid lock 23, a central processor (CPU) (not shown), a timer clock 5, a CR push button 7, a slide gate 11, a battery 13, a medication unit (pill or other) outlet 15, an outlet chamber 17 located within slide gate 11 for receiving a medication dose (med unit), med unit sensor 19 and an optional indicator light 9. The top of dispenser 1 is clear plastic so that a user can see the medication units and their movement. If the entire top is not clear, in preferred embodiments, minimally the path area of the medication to and into the outlet chamber 17 of gate 11 should be clear. Otherwise, a user may rely upon gravity to tilt to load the outlet chamber 17 by feel and sound. Thus, a user must tilt dispenser 1 until the user sees a medication dosage load into outlet chamber 17. Next, the user will push the CR (child resistant) push button 7, wait for indicator light 9 to turn on, and then move the slide gate 11 to dispense the medication dose. However, med unit sensor 19 must sense a med unit, or solenoid lock 25 will not unlock and gate 11 will not dispense. Thus, the sensor 19 feedback to the CPU affords an override to stop the gate if no med is sensed in the outlet chamber 17. Conversely, if a med unit is sensed, and the CPU timer is in the "permitting" time frame, the solenoid lock 25 will open and gate 11 may be slid to a dispensing position so that the med unit may now be procured by the user via outlet 15. Then, the CPU will reset and a countdown will be displayed on timer clock 5, counting down to the next appropriate time to dispense medication. This is repeated until a refill is required, as discussed below.

FIGS. 2, 3, 4, 5, 6 and 7 show partially blown top cut views of another embodiment of a present invention programmable, refillable medication dispenser with scheduled metered medication unit dispensing that show more details of the locks, solenoids, cartridge and sensor in different steps during use. Identical parts are identically numbered throughout these drawings, as well as subsequent drawings below, and are thus not repeated in their entirety for each drawing. Here present invention device 30 has a main housing 40, a countdown clock 36 connected to CPU 38, a red/green light 33, such as an LED, that goes from red to green when dispensing is permitted, a dispensing slide gate 31 with outlet chamber 32, a cartridge locking solenoid locking piston (like that shown in Figure1, but not shown here), a gate locking solenoid and piston 35, and cartridge 37, and exit orifice 39. Also, there is sensor 43 that senses med unit presence in the chamber and send signal feedback to CPU 38. This device has been loaded with cartridge 37 by a pharmacist who has also set the time in the CPU memory in accordance with a prescription dosage regimen. The user patient waits until the countdown goes to zero, aligns a pill, tablet, capsule or other medication with the outlet chamber 32 and uses gravity to drop it into the outlet chamber 32, and then slides the gate 31 to release a medication dosage, provided that sensors 43 and 50 see a med unit in the chamber. The gate 31 (or elsewhere on the device) may optionally carry a legend, such as "SLIDE HERE" with an arrow, to show the patient which part to move for dispensing.

Figure 2:
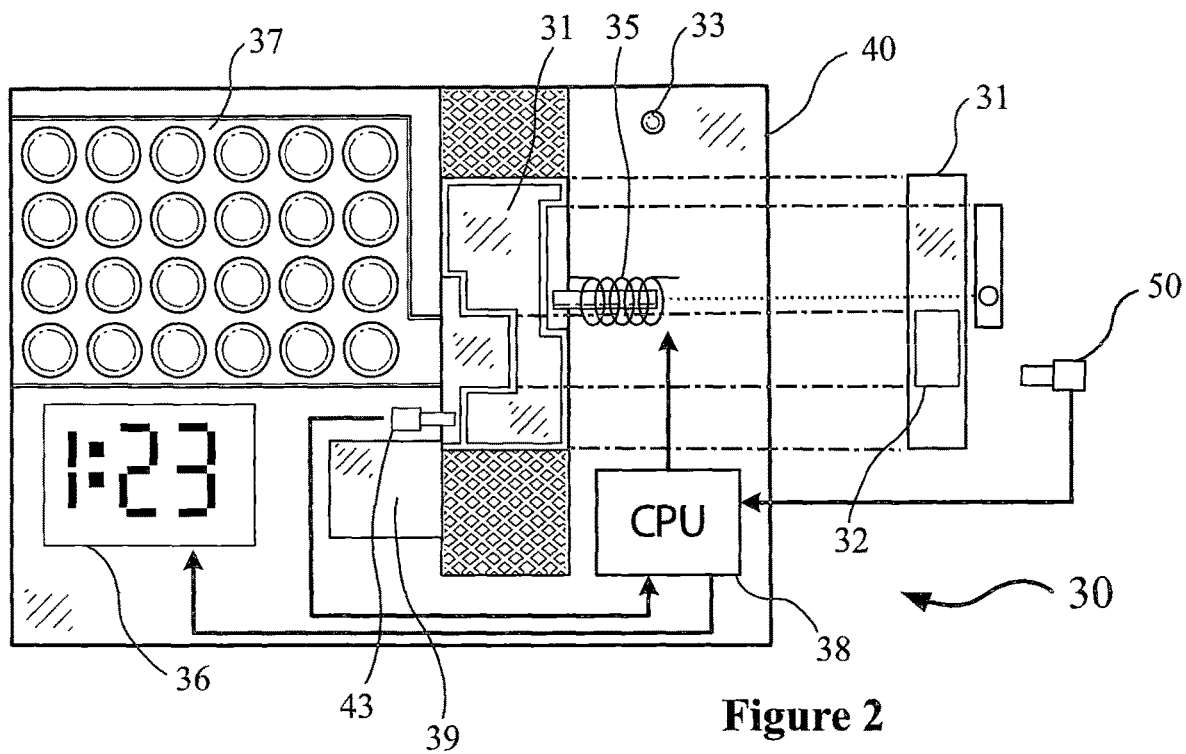
FIGS. 2 through 7 show top views of another embodiment of a present invention programmable, refillable medication dispenser with sensing and scheduled metered medication unit dispensing, illustrating each sequential step taken to achieve dispensing.
Figure 3:
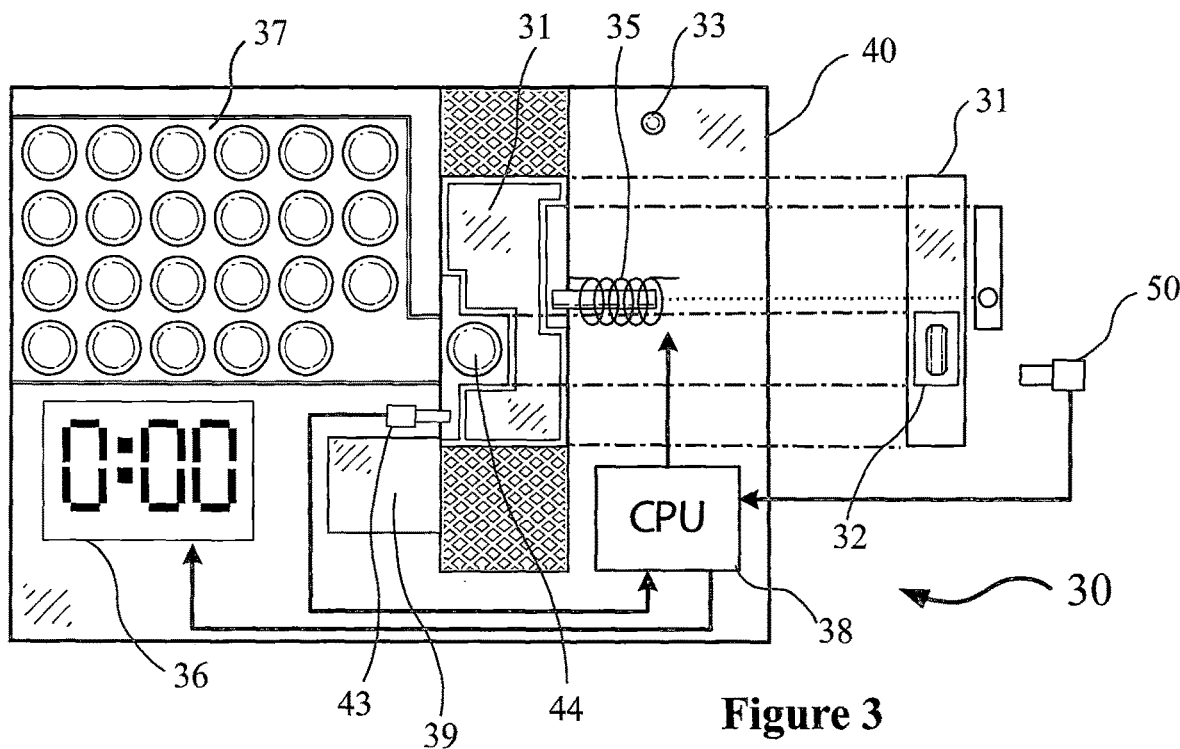

Referring to specifics of these FIGS. 2 through 7, FIG. 2 shows device 30 in its inoperable mode, i.e., clock 36 has not yet counted down to zero for a pill to be released and thus, a user cannot slide gate 31 to its dispensing position. It is in the "prohibiting time" of the timer sequence. FIG. 3 shows that clock 36 has counted down to zero with light 33 turning green, and it is now in the "permitting time" for dispensing. In this FIG. 3, the user has taken advantage of this dispensing opportunity by tilting to move the pill 44 into outlet chamber 32 of gate 31, a first step to successful dispensing. (This move could have been made when the clock has not run down to zero, but further action to dispense would be stopped (prohibiting time).

Figure 4:
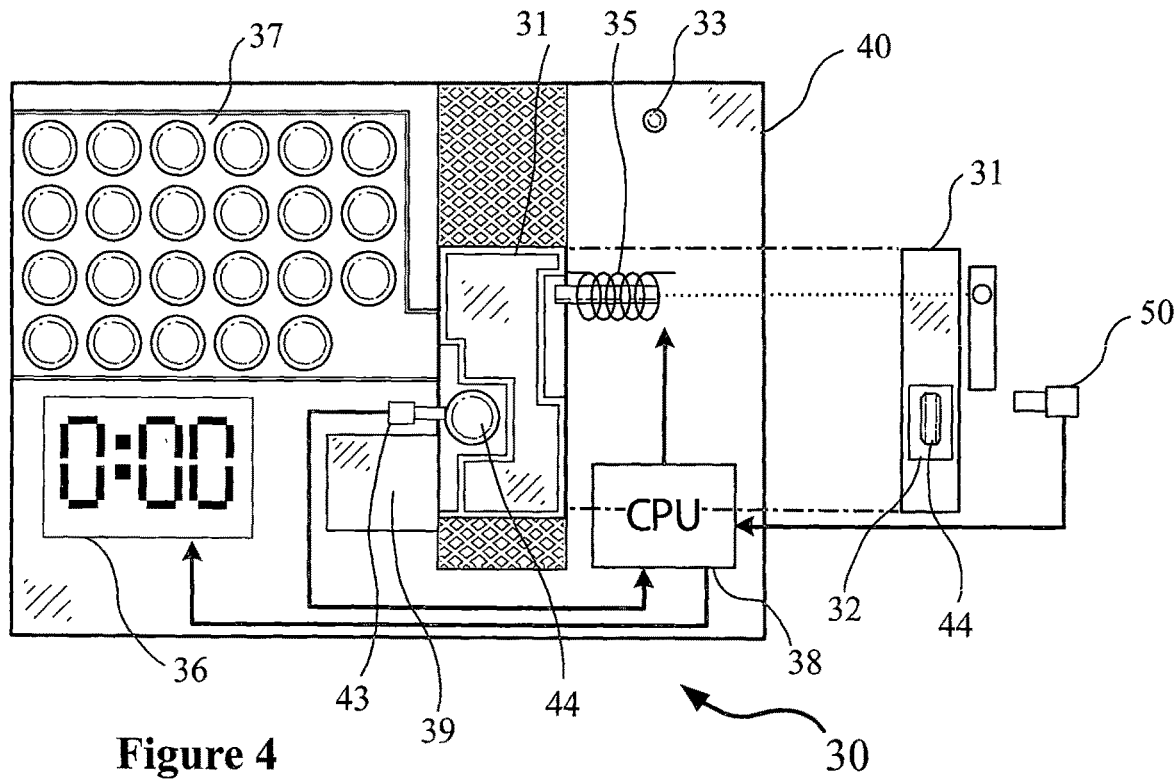
Figure 5:
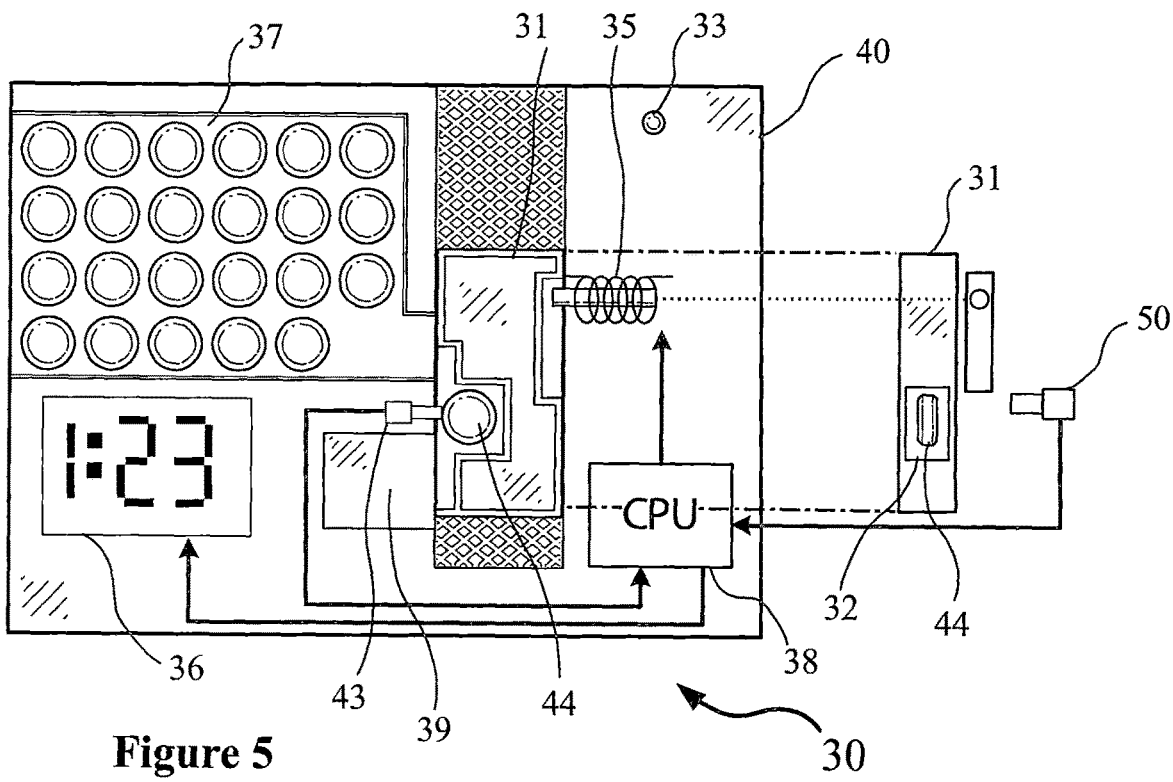
Figure 6:
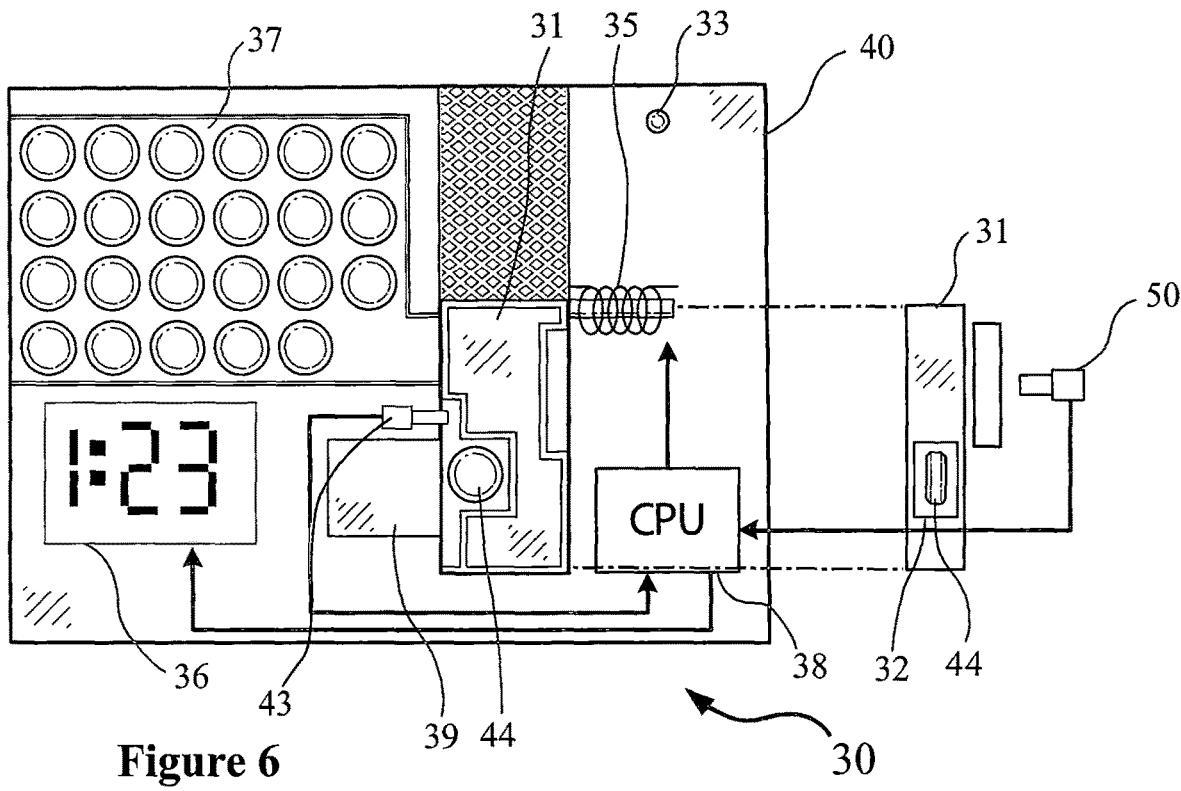
Figure 7:
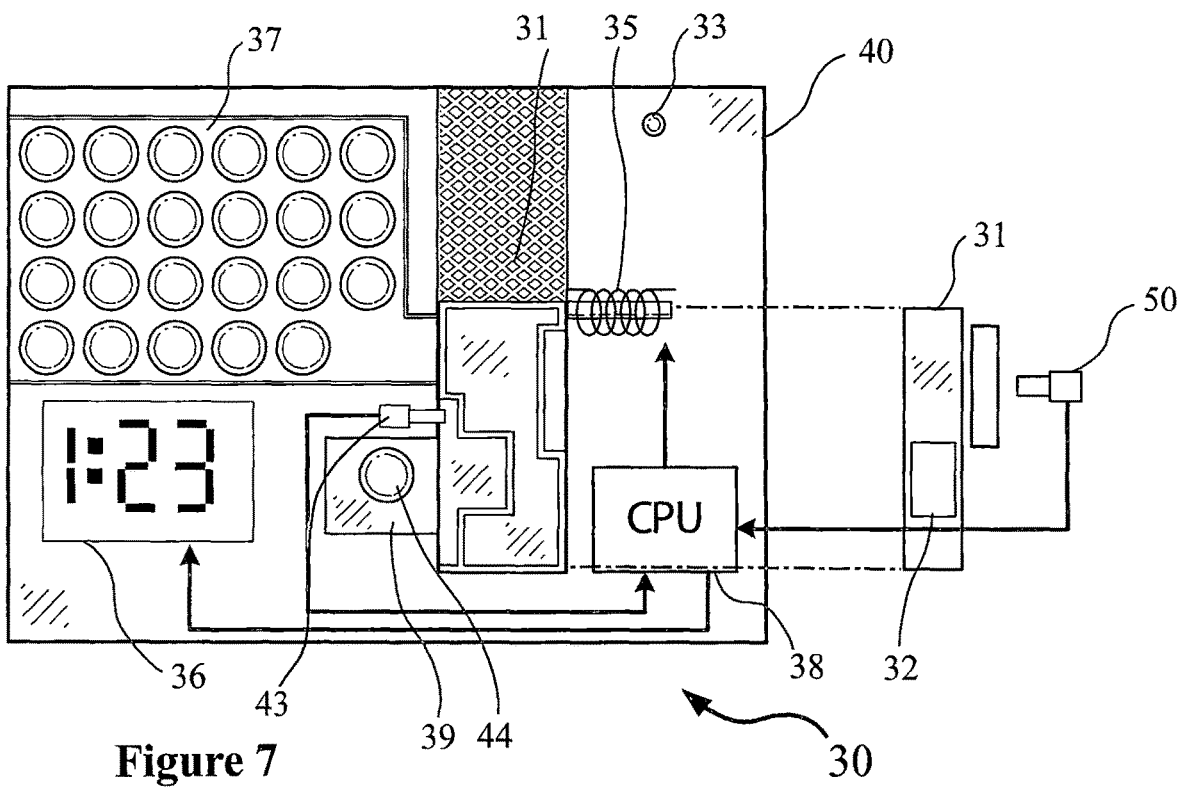

In FIG. 4, the user has moved slide gate 31 partially down, at which point sensors 43 and 50 detect pill 44 in the chamber 32. When this occurs, gate locking solenoid and piston 35 is retracted (opened), shown in FIG. 5, because both the timer clock is in the permitting time and the sensor(s) see the pill 44 in the chamber. Also, the gate may be moved to its fully opened position to release the pill 44 from the chamber to the outlet 39. This is shown in FIG. 6. Also, the timer may be reset here to begin a new countdown. In FIG. 6, because the locking solenoid and piston is in the unlocked position, the user is able to slide the gate 31 further down so that pill 44 is properly aligned with exit outlet 39. In FIG. 7, the user moves the pill 44 to the outlet 39 and dumps the pill out for consumption.

Figure 8:
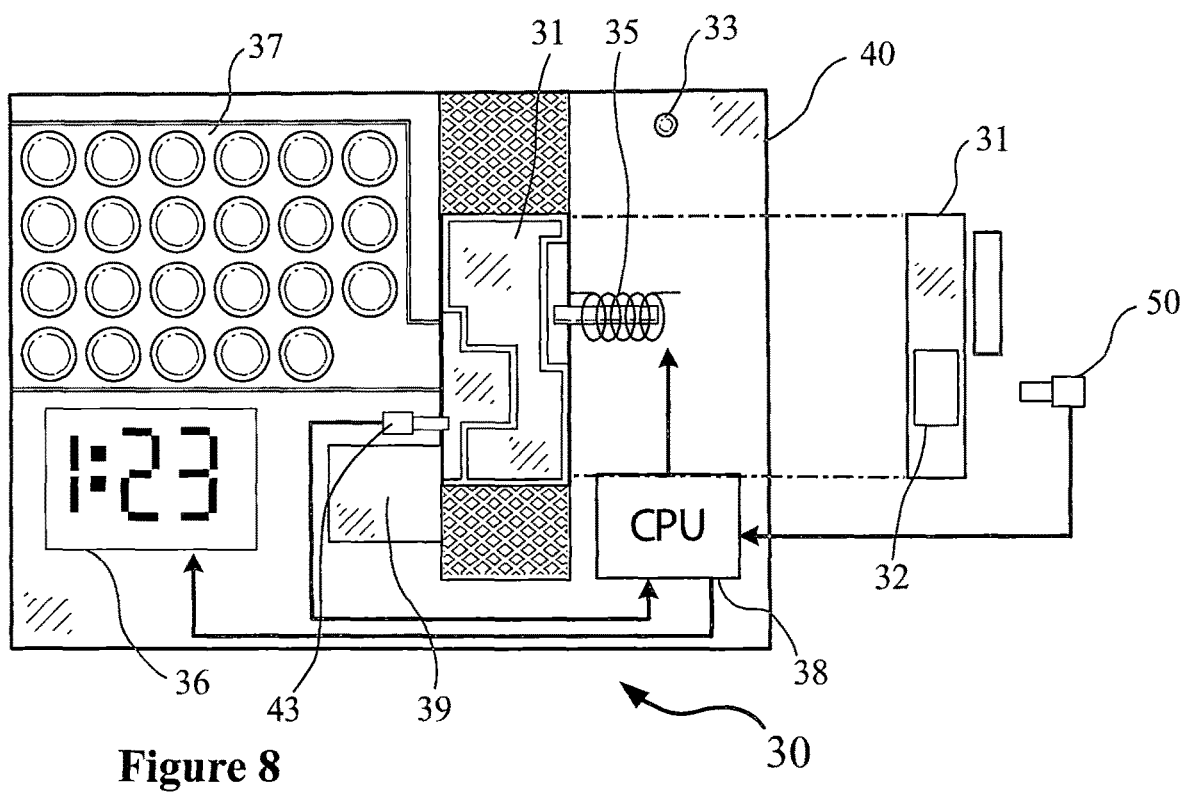
FIG. 8 shows a present invention device from the foregoing Figures, but after a pill is dispensed and before the gate is reset.

FIG. 8 shows device 30 anytime after the pill 44 is taken and before the countdown again reaches zero and while the gate is still in its dispensing position. Here, the slide gate 31 upper portion blocks movement of another pill into the chamber until the gate 31 is pushed up to its original position (which is known to the CPU through sensor 50), at which time the piston locks it until the two required conditions described above are met-timer goes to zero and sensor sees a med unit in the chamber.

Figure 9:
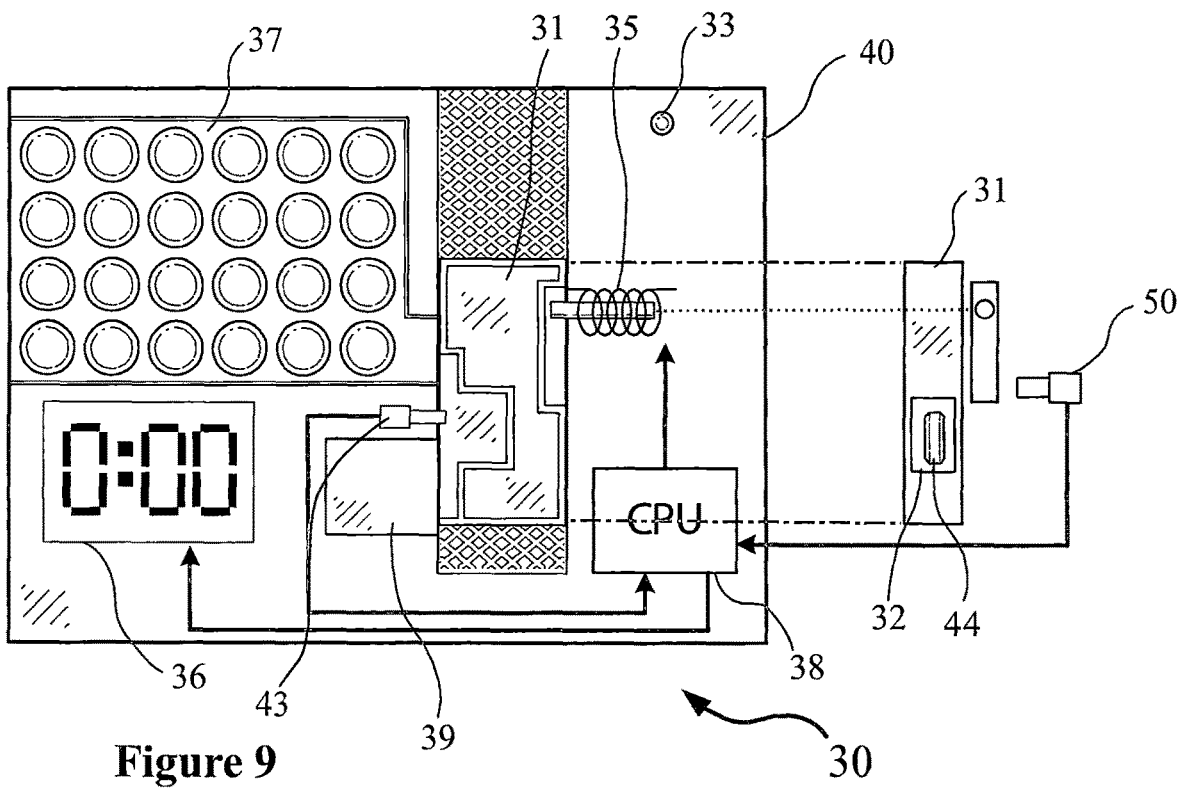
FIG. 9 illustrates a false start therewith.

FIG. 9 illustrates a false start by a user, wherein the user fails to or forgets to move a pill into the outlet chamber 32. In this case, the sensor 43 sees no pill and prohibit (stop) any further effort to dispense.

Figure 10:
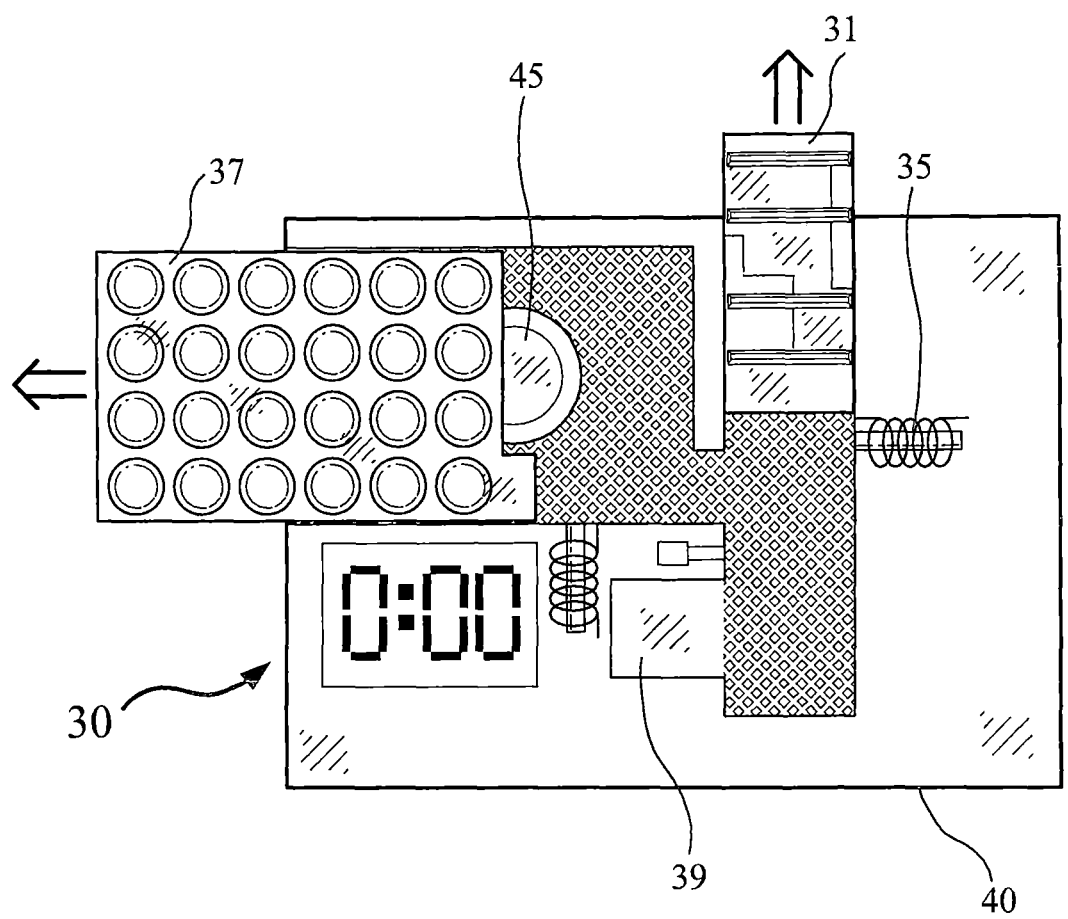
FIG. 10 shows a present invention device with a cartridge partially removed to show an otherwise unreachable battery.

FIG. 10 shows that when a pharmacist or other authorized person unlocks the cartridge lock and slides it from the housing, only then is the battery accessible, that is, revealed for possible replacement or removal. In this mode the cartridge 37 may be replaced with the same or different medication. Also, the slide gate 31 is now removable and may be replaced with a different size chamber-gate to accommodate different size or shape medication.

Figure 11:
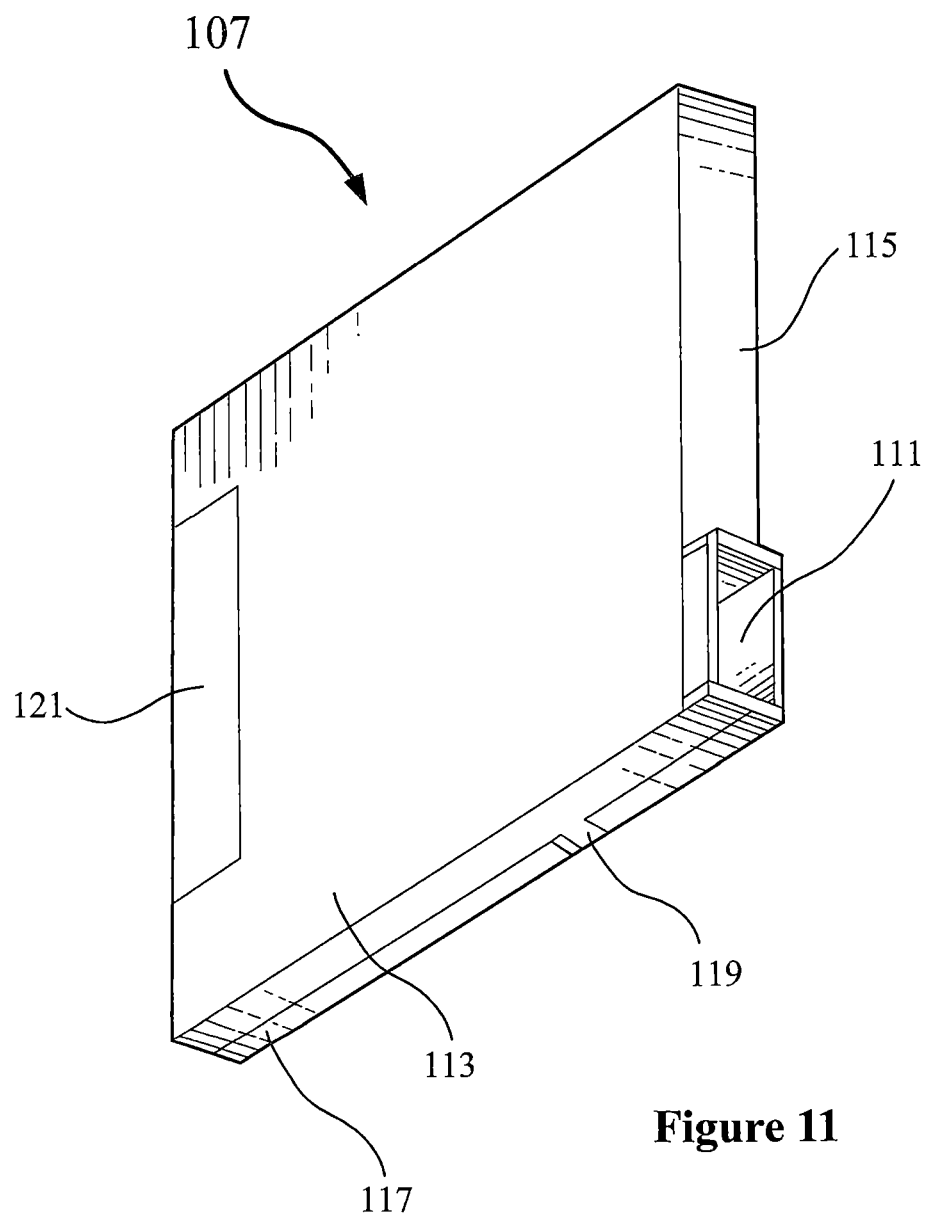
FIG. 11 shows an oblique view of one preferred cartridge used in present invention devices.

FIG. 11 shows details of the medication cartridge 107 in some of the previous Figures. Cartridge 107 includes a housing with a top 113 with grip 121, a side 117, with a piston lock receiver slot 119 and a front 115 with a dispensing orifice 111 that would align with the toggle chute of dispenser 101. There are two locks, not shown, in this arrangement, one to lock the gate until the timer counts down to zero, and the sensor sees a pill in the outlet chamber, at which time the solenoid for that lock would be activated to retract the piston lock to permit gate movement to dispense, and a second lock to retain the cartridge 107 in the dispenser until a pharmacist or other professional desired access to fill or refill a prescription.

Figure 12:
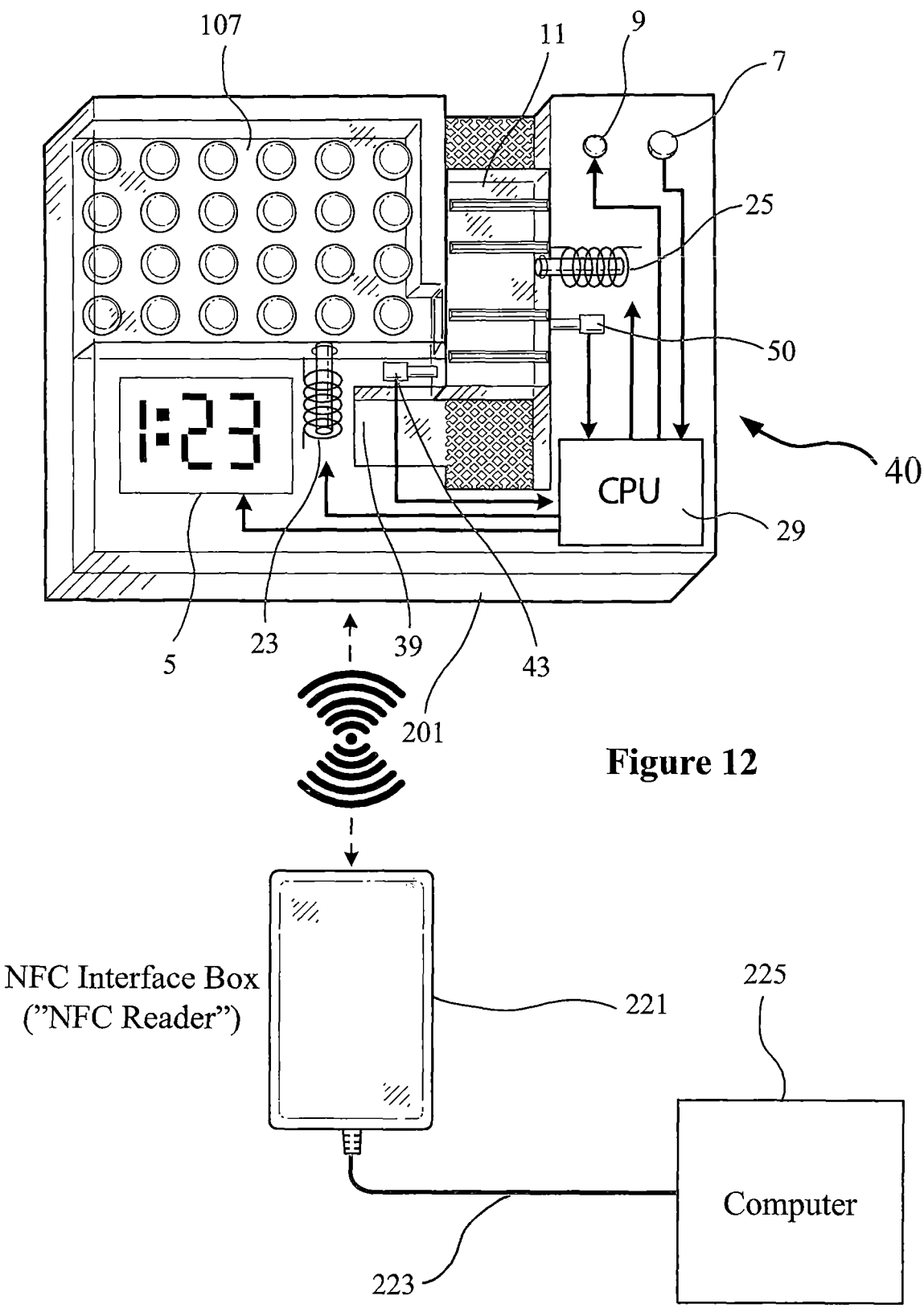
FIG. 12 shows a present invention device such as are shown previously, but with wireless communications capabilities.

FIG. 12 shows a top view of the present invention programmable, refillable medication dispensers with scheduled metered medication unit sensing and dispensing, in the context of system components used at a control point, such as a pharmacy or nursing home or opioid dispensary with wireless communications. Present invention dispenser 40 has the same components as the present invention device shown in FIG. 1, except that the CPU 29 is shown and has transmitter/receiver subcomponents. This device 40 also has sensor 43 as shown in FIG. 2 et seq. In this version of the present invention dispenser 40, the battery is also locked by being blocked by the cartridge, which makes the system more secure in that only the pharmacist or other authorized party can remove/replace the battery.

In FIG. 12, there is also a desktop (or other computer) 225, used by the pharmacist, with connection 223 to an NFC (non-contact frequency connector, aka near-field communication) reader 221. This reader establishes a wireless connection between the computer 225 and the dispenser 201, so that the pharmacist can unlock the cartridge, refill it, program the dispenser CPU and reset the time in accordance with the patient's prescription. It should be noted that this arrangement may also include a battery (and/or other energy storage components) recharge step using wireless recharging of the dispenser's battery (or another component, such as a pharmacist-enabling capacitor).

Figure 13:
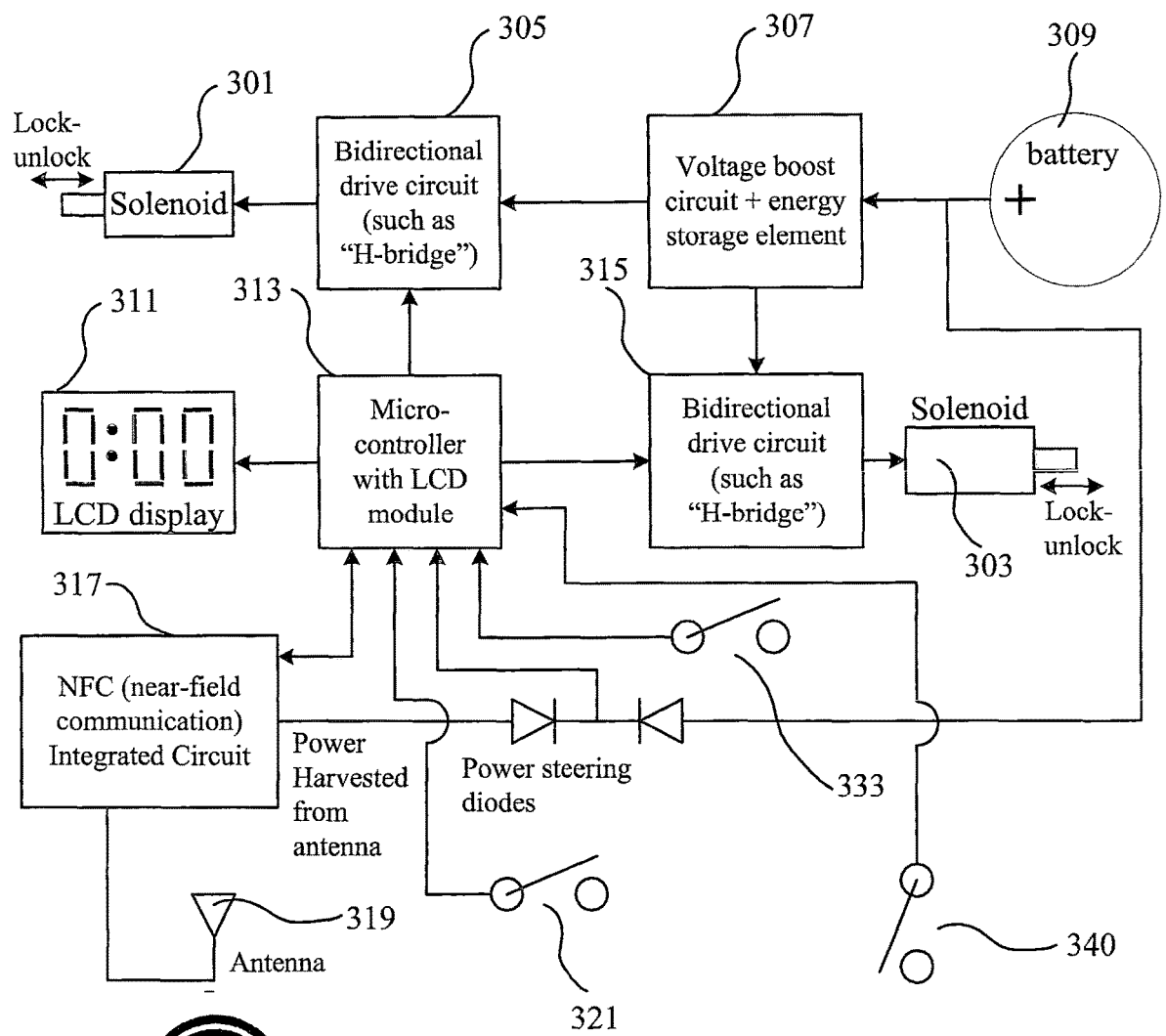
FIG. 13 shows a block diagram of an embodiment of the present invention device as used in conjunction with a communications device (NFC Reader) and a programming computer, such as are shown in FIG. 12.
Figure 13:
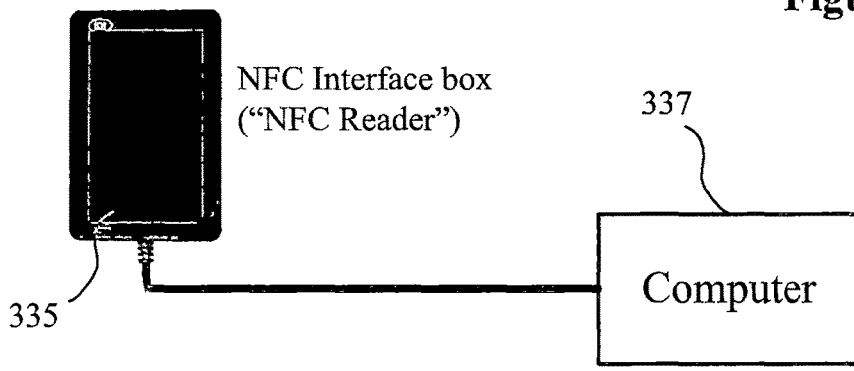

FIG. 13 shows a block diagram of an embodiment of the present invention device as used in conjunction with a communications device (NFC Reader) and a programming computer, such as are shown in FIG. 12. This diagram excludes the cartridge main housing, the gate and the cartridge, but the components are positioned to be consistent with the prior drawings that show these missing components. Solenoid 301 is used to lock and unlock the cartridge for filling or refilling a prescription. It is controlled by a voltage boost circuit 307 connected to battery 309, and by the microcontroller module 313 and bidirectional drive circuit 305.

In FIG. 13, solenoid 303 is used to lock and unlock the gate, such as a slide gate, toggle or swivel gate, or lidded gate dispensing chamber, in accordance with clock 311. It is controlled by the microcontroller with LCD module 313, including its internal, programmed dispensing clock (countdown displayed by clock 311), by a voltage boost circuit 307 connected to battery 309, by bidirectional drive circuit 315 and by sensor button 333. Module 313 is also connected to NFC circuit 317, which in turn receives power and instructions from NFC reader 335, connected to computer 337. There is also a CR button 321 and power steering diodes 323 and 325. (Note that to connect the pharmacist's computer to the dispensing device for communications, programming and time setting, alternatives and equivalents could be used in place of the NFC interface device, such as WiFi, Blue Tooth, USB connector or other wireless or wire-based connections.)

FIGS. 14A, 14B, 14C and 14D show a flow diagram of the steps involved in the utilization of other embodiments of the present invention programmable, refillable medication dispensers with scheduled metered medication unit dispensing.

Figure 14A:
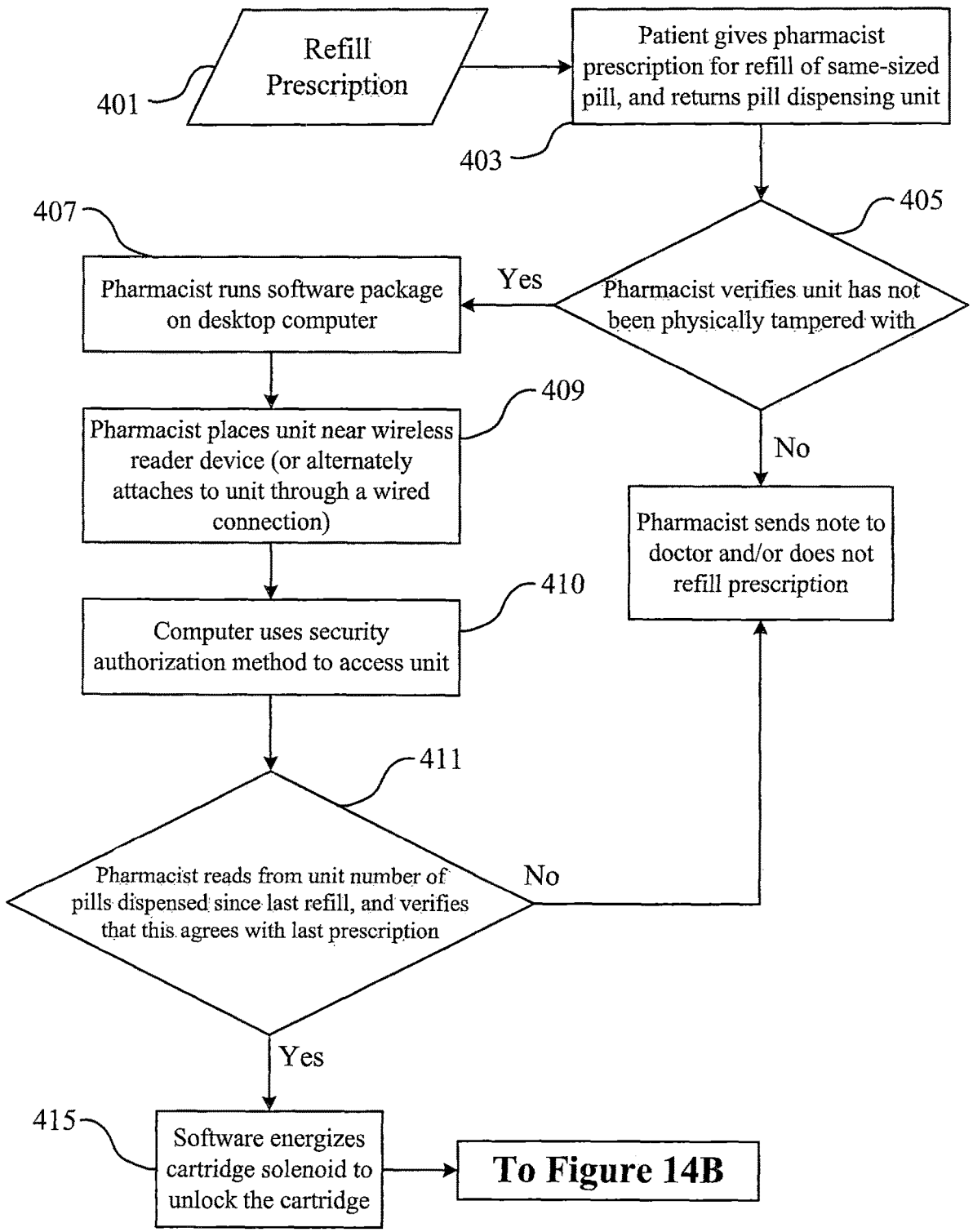
FIGS. 14A, 14B, 14C and 14D show a flow diagram of the steps involved in the utilization of other embodiments of the present invention programmable, refillable medication dispensers with sensing and scheduled metered medication unit dispensing.

In FIG. 14A, the user has exhausted the medication in a present invention dispenser, such as those described elsewhere herein, and seeks to refill the prescription, block 401. The patient delivers the dispenser to the pharmacist or other dispensary for a refill of the same medication (same formulation and same size pill or tablet), block 403. The pharmacist verifies that the dispenser has not been damaged or tampered with, block 405. If yes, it has not been damaged or tampered with, proceed to block 407. If it has been damaged or tampered with, the pharmacist does not refill the prescription and notifies the prescribing doctor, block 413, wherein the doctor may require a visit by the patient before rewriting, refuse to rewrite, make alternative recommendations to the user, such as rehab, etc. If the dispenser has not been damaged or tampered with, the pharmacist uses the related software on his computer (which may be his phone, laptop, desktop, notebook or other PDA), block 407. The pharmacist connects the dispenser to his computer (wirelessly or by wire connection), block 409. At this point, the pharmacist uses security authorizations to access the dispenser, block 410. This is an alternative to above and may involve one or more than one security step. There is recognition of the device to the pharmacist's software package, and this involves CPU identification. Here, there may also be a systems security aspect, such as independent verification of the authenticity of the prescription. For example, regional hospitals now link with doctors in their area and share patient information (in a HIPPA-compliant manner). In that way, a general practitioner, a pain management doctor, an orthopedist and a treating psychologist may all simultaneously know that the patient is getting a refill. Next, the pharmacist confirms the number dosages to be dispensed and verifies it, block 411. If the confirmation is not correct, then return to block 413, as elaborated upon above. In some cases of the present invention devices, as here, the cartridge is unlocked by energizing the cartridge solenoid at the time of need, to save battery life. Thus, the next step, energizing the cartridge solenoid, is automatically done by the software upon confirmation by the pharmacist, block 415. Next steps are shown in the next Figure.

Figure 14B:
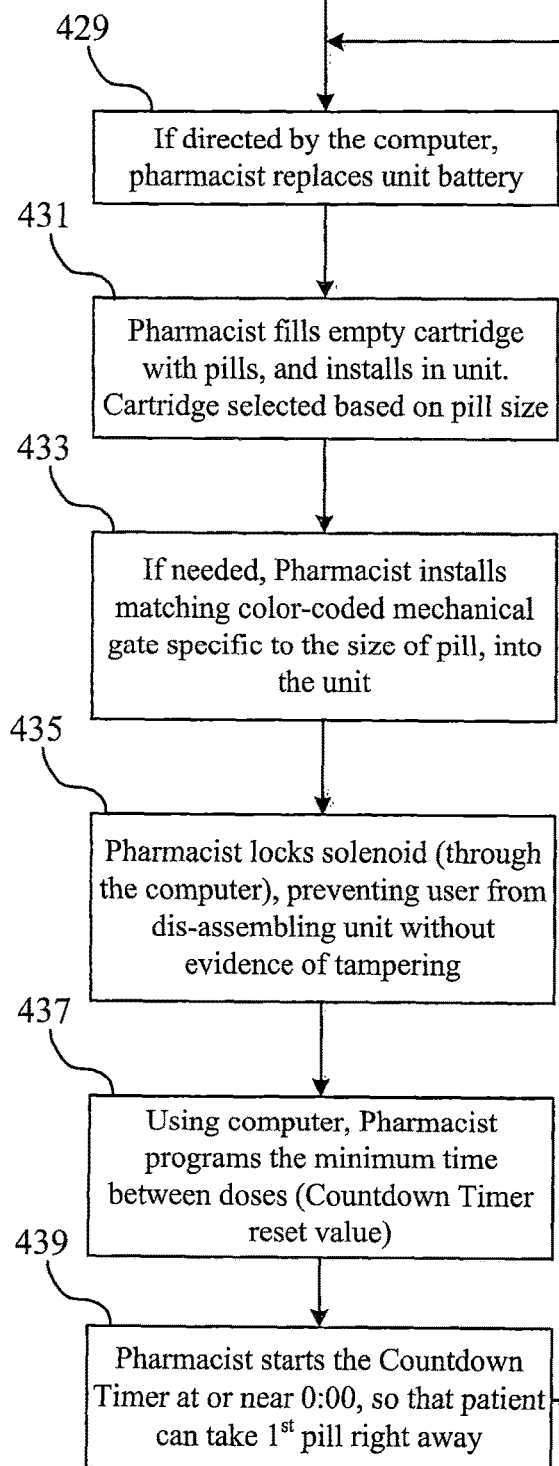
Figure 14B:
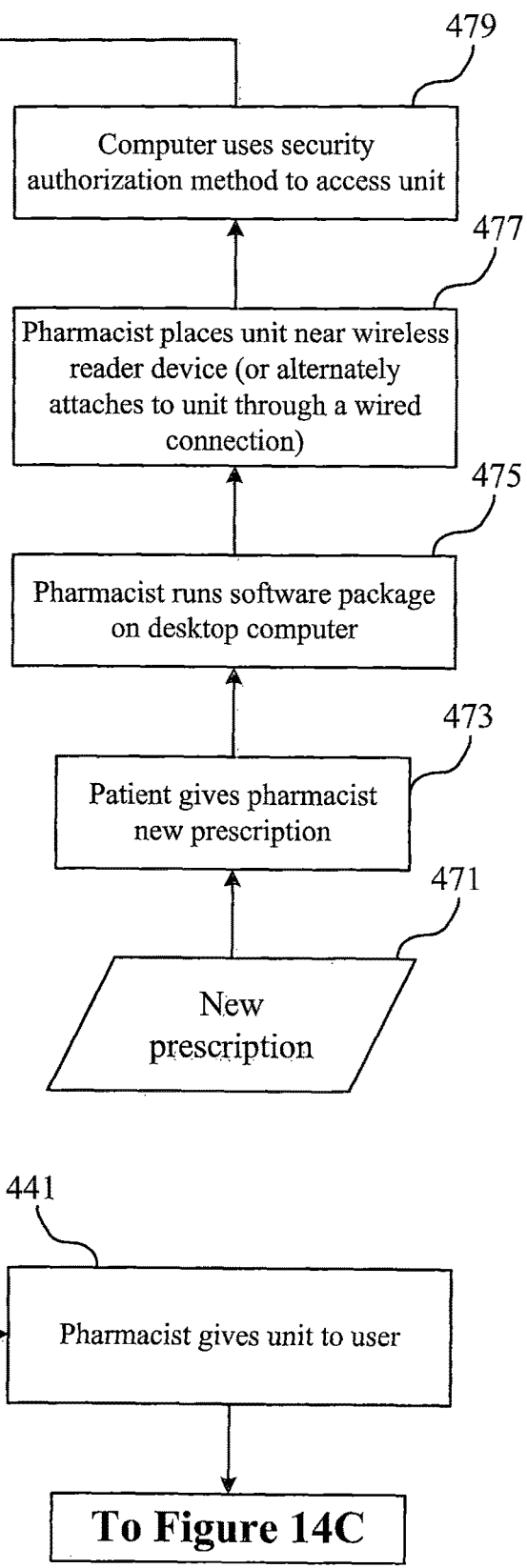

FIG. 14B, left column, these next steps are sequential. As an optional feature, the computer may "read" the battery and recommend a recharge or a battery replacement, block 429. The pharmacist fills the empty cartridge with the correct quantity of medication, such as pills, and returns the filled cartridge (or a replacement cartridge) to the dispenser unit, block 431. If needed, a new gate may also be inserted (if, for example, the pill size has been changed by the manufacturer or the doctor has increased or decreased individual dosages: example, warfarin 5 mg is much larger than warfarin 1 mg), block 433. The cartridge is locked in by the computer signal initiated by the pharmacist, block 435. The pharmacist now programs the dispenser unit for the correct time lapse between dosages or confirms existing countdown settings, Countdown Timer reset value, block 437. The pharmacist may set the countdown timer at zero to allow the user patient to take a dose right away, if appropriate, block 439, and gives the dispenser unit to the user patient, block 441.

FIG. 14B, right column, shows an additional set of pre-steps for a new prescription, at block 471 and up the column. Here, the patient gives the pharmacist a new prescription, block 473, and he rims the software package, and in some programs, inputs patient information, other id information (such as a hospital portal link) and the prescription, block 475. He may also check a connected or separate data base to see if there are any conflicts (such as the same script being filled yesterday at another pharmacy!). Next, he connects a new dispenser unit to his computer, either by wire or wirelessly, block 477, and obtains security authorization to proceed, block 479. The subsequent steps are already discussed above and these are set forth in blocks 429 through 441, supra.

Figure 14C:
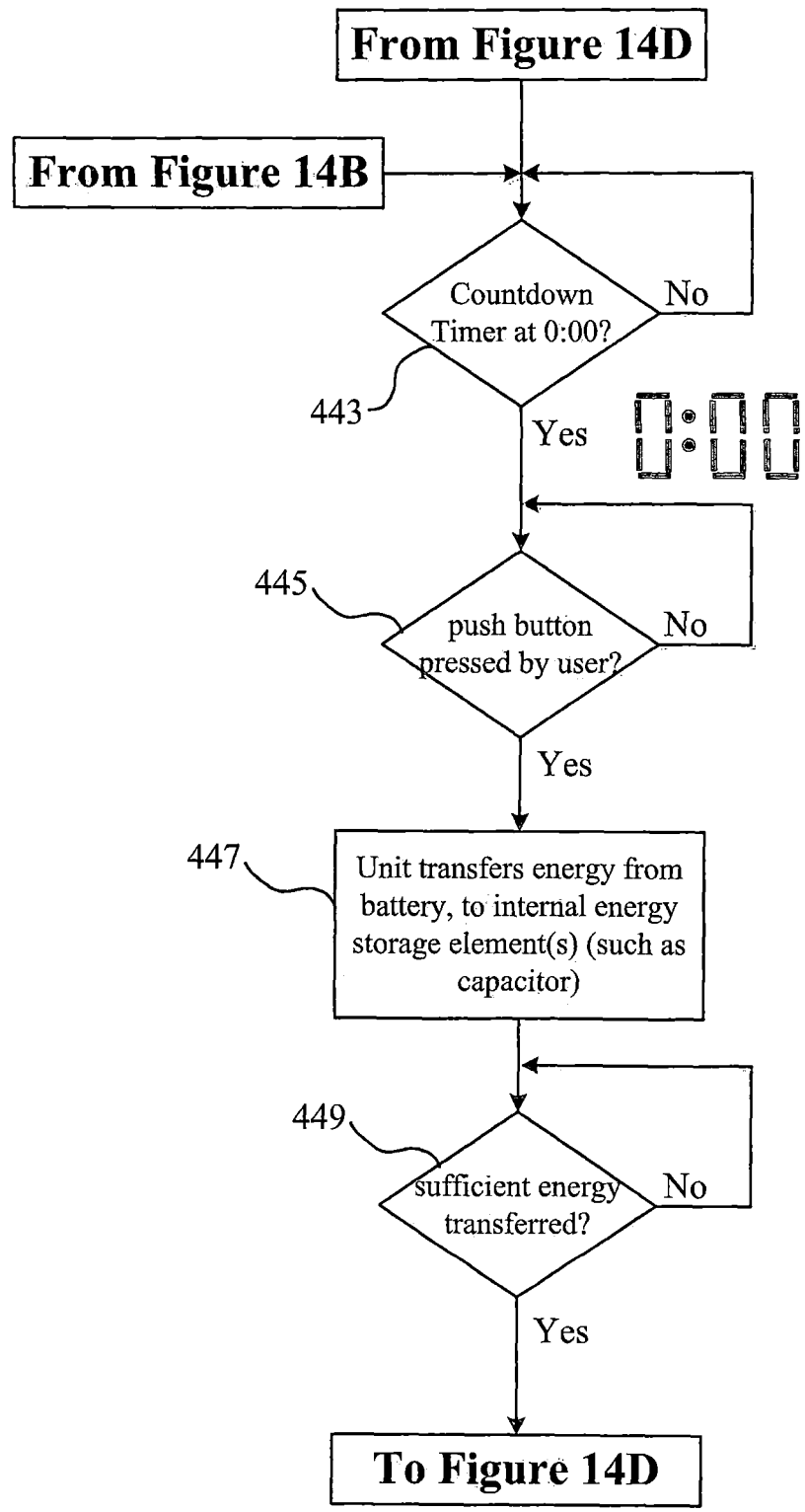
Figure 14D:
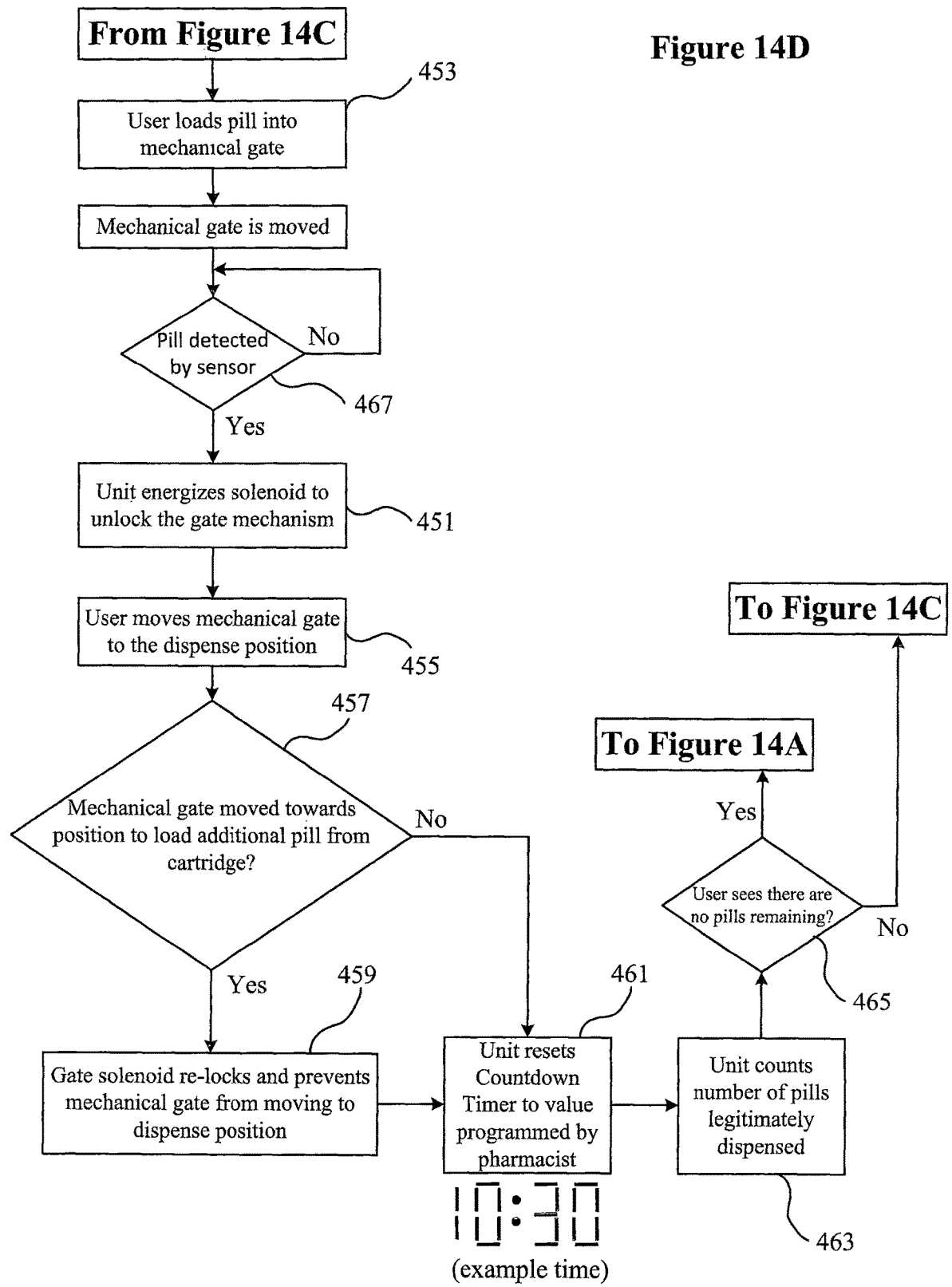

FIGS. 14C and 14D continue the flow diagram, are now discussed together, and address the steps involved after the patient has received his dispenser with medication. Is the countdown timer at zero, block 443? If not, the user must wait until it counts down to zero. When it is at zero, the user pushes the outside button, block 445, to initiate power from the battery to internal storage elements, block 447. The user patient loads medication into the outlet chamber of the gate by gravity by rotation, block 453. Next, medication detecting sensor 467 determines whether the user has properly moved a med unit into the gate outlet chamber, and, if not, the user must try again. If so, then the gate is unlocked, block 451. Next, the user dispenses the medication by moving the gate, block 455. The gate then is returned to its rest position, block 457, wherein the toggle relocks by automatic solenoid activation, block 459, it cannot be used until the next countdown is completed. The countdown timer is reset in accordance with the programming set by the pharmacist, block 461. The dispenser unit may keep count of the number of pills dispensed, block 463, and when there are no pills remaining, block 465, the user patient commences the refill steps as set forth above.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims. For example, the actual shape of the main housing may be any of numerous possibilities as long as its functionality as described is not affected adversely.

What is claimed is:

1. A programmable, refillable medication dispenser with scheduled metered medication unit dispensing, which comprises:
   a) a main housing having an outer structure and a cartridge receiver for insertion and removal of a multi-unit medication cartridge, said cartridge receiver being positioned for alignment of said multi-unit medication cartridge with a medication outlet chamber;
   b) a medication outlet chamber within said main housing, with a medication outlet for controllably releasing a medication unit from said cartridge and from said chamber according to a programmed schedule;
   c) a medication unit sensor functionally connected to said medication outlet chamber and connected to a powered, programmable central processing unit;
   d) a reusable, refillable multi-unit medication cartridge positioned in said cartridge receiver, said cartridge containing a plurality of free flowing medication units for gravity feed dispensing, and having a cartridge lock receiver and a dispensing orifice, said free flowing medication units being solid medication units selected from pills, tablets and capsules;
   e) said powered, programmable central processing unit located in said main housing that includes sufficient hardware and software to include a programmable timer for scheduled permitting time and scheduled prohibiting time for dispensing a medication unit from said medication outlet chamber, and includes an override subprogram connected to said medication unit sensor wherein a medication unit can only be dispensed by the opening of a medication release control gate when both said timer is operating in a permitting time and a medication unit is sensed in said medication outlet chamber by said sensor, and when either a medication unit is not sensed or when said timer is operating in a prohibiting time, said release control gate cannot be opened;
   f) a multi-unit medication cartridge lock functionally connected to said central processing unit and positioned adjacent to said cartridge receiver for locking and unlocking a cartridge;
   g) a gate control mechanism and said medication release control gate connected to said gate control mechanism, said medication release control gate being positioned at said outlet, and said control gate having a first position prohibiting medication unit dispensing by closing said gate when said timer is in a prohibiting time or when there is no medication unit sensed in said chamber, or both, and a second position permitting medication unit dispensing by opening said gate when said timer is in a permitting time and a medication unit is sensed in said chamber by said sensor;
   h) a power source connected to said programmable central processing unit;
      wherein, an authorized medication dispensing person will insert and lock a multi-unit medication cartridge into said cartridge receiver of said main housing and will program said central processing unit to permit a patient user to move a medication unit into said outlet chamber and to accomplish dispensing activation according to a predetermined schedule such that when medication dispensing is permitted and a medication unit is sensed in said chamber, said gate control mechanism may be activated and said control gate may be opened for dispensing, and when medication dispensing is prohibited or a medication unit is not sensed in said chamber, said gate control mechanism cannot be activated.

2. The programmable, refillable medication dispenser with scheduled metered medication unit dispensing of claim 1 which further includes an externally exposed operate-indicator that has a first setting to indicate that said dispenser is inoperable and a second setting to indicate that said dispenser is operable for controllably releasing a medication unit from said dispenser.

3. The programmable, refillable medication dispenser with scheduled metered medication unit dispensing of claim 2 wherein said indicator is selected from the group consisting of a visual indicator, and an audio indicator and combinations thereof.

4. The programmable, refillable medication dispenser with scheduled metered medication unit dispensing of claim 1 wherein said multi-unit medication cartridge lock includes a solenoid and lock bar having an extended lock position and a retracted unlock position, and in wherein said solenoid is functionally connected to said central processing unit.

5. The programmable, refillable medication dispenser with scheduled metered medication unit dispensing of claim 1 wherein said medication release control gate includes a gate wall, and said gate control mechanism is a gate solenoid that is functionally connected to said gate, said solenoid having a push bar that is operable only when said timer is in a permitting time and a medication unit is sensed in said chamber, said push bar having an extended position maintaining a locked gate and having a retracted position maintaining an unlocked gate.

6. The programmable, refillable medication dispenser with scheduled metered medication unit dispensing of claim 1 wherein said medication release control gate is selected from the group consisting of a slide gate, a rotatable gate, a toggle gate and a hinged gate.

7. The programmable, refillable medication dispenser with scheduled metered medication unit dispensing of claim 6 wherein said gate is a slide gate.

8. The programmable, refillable medication dispenser with scheduled metered medication unit dispensing of claim 1 wherein there is further i) at least one patient user control component connected to said central processing unit and externally exposed for user dispensing activation that functions as a child resistant feature that must be activated to move said gate control mechanism to its second position, to permit medication unit dispensing by opening said gate.

9. The programmable, refillable medication dispenser with scheduled metered medication unit dispensing of claim 8 wherein said patient user dispensing control component is a button and said button operates in conjunction with said gate as a child resistant feature that must be activated to dispense medication.

10. The programmable, refillable medication dispenser with scheduled metered medication unit dispensing of claim 1 wherein there is a spring mechanism connected to said gate that biases said gate to its closed position.

11. A programmable, refillable medication dispenser with scheduled metered medication unit dispensing, which comprises:
   a) a main housing having an outer structure and a cartridge receiver for insertion and removal of a multi-unit medication cartridge, said cartridge receiver being positioned for alignment of said multi-unit medication cartridge with a medication outlet chamber;
   b) a medication outlet chamber within said main housing, with a medication outlet for controllably releasing a medication unit from said cartridge and from said chamber according to a programmed schedule;

c) a medication unit sensor functionally connected to said medication outlet chamber and to a powered, programmable central processing unit;

d) a reusable, refillable multi-unit medication cartridge positioned in said cartridge receiver, said cartridge containing a plurality of free flowing medication units for gravity feed dispensing, and having a cartridge lock receiver and a dispensing orifice, said free flowing medication units being solid medication units selected from pills, tablets and capsules;

e) said powered, programmable central processing unit located in said main housing that includes sufficient hardware and software to include a programmable timer for scheduled permitting time and scheduled prohibiting time for dispensing a medication unit from said medication outlet chamber, and includes an override subprogram connected to said medication unit sensor wherein a medication unit can only be dispensed by the opening of a medication release control gate when both a medication unit is sensed in said medication outlet chamber by said sensor, and said timer is operating in a permitting time, and when either a medication unit is not sensed or when said timer is operating in a prohibiting time, said release control gate cannot be opened;

f) a multi-unit medication cartridge lock functionally connected to said central processing unit and positioned adjacent to said cartridge receiver for locking and unlocking a cartridge;

g) a gate control mechanism and said medication release control gate connected to said gate control mechanism, said medication release control gate being positioned at said outlet, and said control gate having a first position prohibiting medication unit dispensing by closing said gate when said timer is in a prohibiting time or when there is no medication unit sensed in said chamber, or both, and a second position permitting medication unit dispensing by opening said gate when said timer is in a permitting time and a medication unit is sensed in said chamber by said sensor;

h) a power source connected to said programmable central processing unit;

i) a communication mechanism connected to said control processing unit and adapted to communicate with a separate programming device for at least performing one of: (a) locking and unlocking a multi-unit medication cartridge; (b) permitting and prohibiting unlock time frames for said timer and (c) coupling a power transmission to said dispenser;

wherein, an authorized medication dispensing person will insert and lock a multi-unit medication cartridge into said cartridge receiver of said main housing and will program said central processing unit to permit a patient user to move a medication unit into said outlet chamber and to accomplish dispensing activation according to a predetermined schedule such that when medication dispensing is permitted and a medication unit is sensed in said chamber, said gate control mechanism may be activated and said control gate may be opened for dispensing, and when medication dispensing is prohibited or a medication unit is not sensed in said chamber, said gate control mechanism cannot be activated.

12. The programmable, refillable medication dispenser with scheduled metered medication unit dispensing of claim 11 wherein said communication mechanism is selected from the group consisting of a wire port and a wireless transmitter receiver.

13. The programmable, refillable medication dispenser with scheduled metered medication unit dispensing of claim 12 wherein said communication mechanism includes both a wire port and a wireless transmitter receiver.

14. The programmable, refillable medication dispenser with scheduled metered medication unit dispensing of claim 11 which further includes an externally exposed operate indicator that has a first setting to indicate that said dispenser is inoperable and a second setting to indicate that said dispenser is operable for controllably releasing a medication unit from said dispenser.

15. The programmable, refillable medication dispenser with scheduled metered medication unit dispensing of claim 14 wherein said indicator is selected from the group consisting of a visual indicator, and an audio indicator and combinations thereof.

16. The programmable, refillable medication dispenser with scheduled metered medication unit dispensing of claim 11 wherein said multi-unit medication cartridge lock includes a solenoid and lock bar having an extended lock position and a retracted unlock position, and in wherein said solenoid is functionally connected to said central processing unit.

17. The programmable, refillable medication dispenser with scheduled metered medication unit dispensing of claim 11 wherein said medication release control gate includes a gate wall, and said gate control mechanism is a gate solenoid that is functionally connected to said gate, said solenoid having a push bar that is operable only when said timer is in a permitting time and a medication unit is sensed in said chamber, said push bar having an extended position maintaining a locked gate and having a retracted position maintaining an unlocked gate.

18. The programmable, refillable medication dispenser with scheduled metered medication unit dispensing of claim 11 wherein said medication release control gate is a slide gate.

19. The programmable, refillable medication dispenser with scheduled metered medication unit dispensing of claim 11 wherein there is further i) at least one patient user control component connected to said central processing unit and externally exposed for user dispensing activation that functions as a child resistant feature that must be activated to move said gate control mechanism to its second position, to permit medication unit dispensing by opening said gate.

20. The programmable, refillable medication dispenser with scheduled metered medication unit dispensing of claim 12 wherein said communication mechanism is a wireless transmitter receiver that includes an NFC reader.

* * * * *